United States Patent
Yao et al.

(10) Patent No.: US 8,178,066 B2
(45) Date of Patent: May 15, 2012

(54) METHOD FOR STABILIZING CALCIUM PHOSPHATES FINE PARTICLES, METHOD FOR MANUFACTURING CALCIUM PHOSPHATES FINE PARTICLES BY USING THE METHOD, AND USE THEREOF

(75) Inventors: Takeshi Yao, Kyoto (JP); Mitsuhiro Hibino, Kyoto (JP); Seiji Yamaguchi, Kyoto (JP); Hidetaka Okada, Kyoto (JP)

(73) Assignee: Kyoto University, Kyoto (JP)

( * ) Notice: Subject to any disclaimer, the term of this patent is extended or adjusted under 35 U.S.C. 154(b) by 506 days.

(21) Appl. No.: 11/990,432

(22) PCT Filed: Aug. 15, 2006

(86) PCT No.: PCT/JP2006/316054
§ 371 (c)(1),
(2), (4) Date: Apr. 8, 2009

(87) PCT Pub. No.: WO2007/020928
PCT Pub. Date: Feb. 22, 2007

(65) Prior Publication Data
US 2010/0210736 A1    Aug. 19, 2010

(30) Foreign Application Priority Data
Aug. 15, 2005    (JP) .................................. 2005-235499

(51) Int. Cl.
*C01B 25/32* (2006.01)
*C30B 17/00* (2006.01)
*C30B 29/14* (2006.01)

(52) U.S. Cl. ........... 423/305; 23/295 R; 23/301; 23/304; 423/308; 436/501

(58) Field of Classification Search .......... 423/305–315; 23/295 R–305 RE; 436/501
See application file for complete search history.

(56) References Cited

U.S. PATENT DOCUMENTS
7,348,060 B2 * 3/2008 Tanaka et al. ................. 428/403

FOREIGN PATENT DOCUMENTS
| JP | 04-187600 | 7/1992 |
| JP | 2001-294411 A | 10/2001 |
| JP | 2002-532375 | 10/2002 |

(Continued)

OTHER PUBLICATIONS

Saujanya et al. "Control of nanoparticle size of fillers by polymer blend technique" 2001, Polymer, 42, p. 2255-2258.*

(Continued)

*Primary Examiner* — Stuart Hendrickson
*Assistant Examiner* — Syed Iqbal
(74) *Attorney, Agent, or Firm* — Nixon & Vanderhye P.C.

(57) ABSTRACT

The present invention provides a method for stabilizing fine particles of calcium phosphates without lowering their solid phase forming activity.
It is possible to stabilize the fine particles of calcium phosphates by stopping the growth of the fine particles formed in an aqueous solution supersaturated with respect to calcium phosphates. More specifically, the fine particles of calcium phosphates were stabilized by lowering the inorganic ion concentration of a fine-particle-forming solution containing fine particles of calcium phosphates by dialysis, ion exchange, dilution, or the like, or by separating the fine particles of calcium phosphates from the fine-particle-forming solution by filtration, centrifuging, or the like.

9 Claims, 15 Drawing Sheets

FOREIGN PATENT DOCUMENTS

| | | |
|---|---|---|
| JP | 2004-081754 A | 3/2004 |
| JP | 2005-59001 A | 3/2005 |
| JP | 2005-097081 | 4/2005 |
| JP | 2005-126335 | 5/2005 |
| JP | 2005126335 A * | 5/2005 |
| WO | WO 0037033 A1 * | 6/2000 |

OTHER PUBLICATIONS

International Search Report for PCT/JP2006/316054 mailed Dec. 12, 2006.

M. Tanahashi et al., "Apatite Coating on Organic Polymers by a Biomimetic Process" J. Am. Ceram. Soc. vol. 77 No. 11 pp. 2805-2808 (1994).

M. Tanahashi et al., "Coating of Apatite Layer on Surfaces of Organic Polymers by a Biomimetic Process" Journal of the Japan Society of Powder and Powder Metallurgy vol. 40 No. 10, pp. 1007-1010 (1993).

T. Kokubo et al. "Apatite-Polymer Composites Prepared by Biomimetic Process: Improvement of Adhesion of Apatite to Polymer by Glow-Discharge Treatment" Bioceramics vol. 6 pp. 327-332 (1993).

M. Tanahashi et al. "Apatite formation on Organic Polymers by Biomimetic Process Using $Na_2O$-$SiO_2$ Glasses as Nucleating Agent" Journal of the Ceramic Society of Japan, vol. 102 No. 9 pp. 822-829 (1994).

M. Tanahashi et al. "Apatite Coated on Organic Polymers by Biomimetic Process: Improvement in Its Adhesion to Substrate by NaOH Treatment" Journal of Applied Biomaterials, vol. 5, pp. 339-347 (1994).

M. Tanahashi et al. "Apatite coated on organic polymers by biomimetic process: improvement in its adhesion to substrate by glow-discharge treatment" Journal of Biomedical Materials Research, vol. 29 pp. 349-357 (1995).

M. Tanahashi et al. "Apatite coated on organic polymers by biomimetic process: improvement in adhesion to substrate by HCl treatment" Journal of Materials Science; Materials in Medicine, vol. 6 pp. 319-326 (1995).

N. Ozawa et al. "Micropattern Formation of Apatite by Combination of Biomimetic Method and Transcription of Resist Pattern" Bioceramics, vol. 14, pp. 123-126 (2002).

N. Ozawa et al. "Micropattern formation of apatite by combination of a biomimetic process and transcription of resist pattern", Journal of Biomedical Materials Research, vol. 62, pp. 579-586 (2002).

N. Ozawa et al. "Micro pattern formation of ceramic thin film by synthesis from aqueous solution using resist pattern as a mold", Solid State Ionics, vol. 151, pp. 79-87 (2002).

N. Ozawa et al. "Formation of Apatite Micro Pattern by Combination of a Biomimetic Process and Transcription of a Resist Pattern" Advances in Science and Technology, vol. 41, pp. 31-38 (2002).

T. Matsumoto et al. "Micropatterning of Apatite by Using CaO-$SiO_2$ Based Glass Powder Dispersed Solution" Bioceramics, vol. 16, pp. 911-914 (2004).

K. Hata et al. "Growth of a Bonelike Apatite Layer on a Substrate by a Biomimetic Process" J. Am. Ceram. Soc. vol. 78 No. 4, pp. 1049-1053 (1995).

K. Hata et al. "Bonelike Apatite Formation on Various Kinds of Ceramics and Metals" Journal of the Ceramic Society of Japan, vol. 109, No. 5, pp. 461-465 (2001).

M. Takahashi et al. "Effect of Substrate on Apatite Formation by a Biomimetic Process" Bioceramics vol. 5, pp. 57-64.

T. Kokubo et al. "Growth of Bone-like Apatite Layer on Various Materials in Simulated Body Fluids" Transaction and Final Program, Fourth World Biomaterials Congress, Apr. 24-28, 1992, International Congress Center, Berlin p. 67 (1992).

T. Kokubo et al. "Apatite Formation on Ceramics, Metals and Polymers Induced by a CaO $SiO_2$ Based Glass in a Simulated Body Fluid" Bioceramics, vol. 4, pp. 113-120 (1991).

Y. Abe et al. "Apatite Coating on Ceramics, Metals and Polymers Utilizing a Biological Process" Journal of Materials Science; Materials in Medicine, vol. 1, pp. 233-238 (1990).

* cited by examiner

| | pH7.00 | pH7.20 | pH7.40 | pH7.60 | pH7.80 | PH8.00 |
|---|---|---|---|---|---|---|
| RIGHT AFTER pH ADJUSTMENT | | | | | | |
| 1 HOUR LATER | | | | | WHITE TURBIDITY | WHITE TURBIDITY |
| 3 HOURS LATER | | | | | | WHITE TURBIDITY AND WHITE PRECIPITATE |
| 6 HOURS LATER | | | | | WHITE TURBIDITY AND WHITE PRECIPITATE | |
| 10 HOURS LATER | | | | | | |
| 28 HOURS LATER | | | | | | |
| 53 HOURS LATER | | | | | | |
| 77 HOURS LATER | | | | WHITE PRECIPITATE | | |
| 149 HOURS LATER | | | | | | |
| 508 HOURS LATER | | | WHITE PRECIPITATE | | | |
| | pH7.00 | pH7.20 | pH7.40 | pH7.60 | pH7.80 | PH8.00 |

| | | JUDGMENT OF TYNDALL PHENOMENON | IMAGE OF TYNDALL PHENOMENON |
|---|---|---|---|
| AT pH ADJUSTMENT (BEFORE ULTRASONIC IRRADIATION) | SAMPLE A | × |  |
| | SAMPLE B | × |  |
| RIGHT AFTER ULTRASONIC IRRADIATION | SAMPLE A | ○ |  |
| | SAMPLE B | × |  |
| 1 HOUR AFTER ULTRASONIC IRRADIATION | SAMPLE A | ○ |  |
| | SAMPLE B | × |  |
| 29 HOURS AFTER ULTRASONIC IRRADIATION | SAMPLE A | ○ |  |
| | SAMPLE B | × |  |

METHOD FOR STABILIZING CALCIUM PHOSPHATES FINE PARTICLES, METHOD FOR MANUFACTURING CALCIUM PHOSPHATES FINE PARTICLES BY USING THE METHOD, AND USE THEREOF

This application is the U.S. national phase of International Application No. PCT/JP2006/316054, filed 15 Aug. 2006, which designated the U.S. and claims priority to Japanese Patent Application No. 2005-235499, filed 15 Aug. 2005, the entire contents of each of which are hereby incorporated by reference.

TECHNICAL FIELD

The present invention relates to a method for stabilizing calcium phosphates fine particles, a method for manufacturing calcium phosphates fine particles, and use thereof, all of which are suitably used for a drug delivery system, a biosensor, a bioreactor, a medical device such as an artificial organ, an electronic device, an optical device, a magnetic material, a biodevice, and others.

BACKGROUND ART

It is known that calcium phosphates have a high affinity with biological materials (e.g. DNAs, proteins, and bones), cells, microorganisms, and the like. Among calcium phosphates, apatites have a bio-affinity. Especially, hydroxyapatites have a high affinity. Further, the hydroxyapatites are known as inorganic components constituting a bone of a living body, together with collagen. The hydroxyapatites have become a focus of attention since they can be used as functional material having biocompatibility (e.g. materials for artificial tooth and artificial bone) because of their living body components and their high affinity.

For example, it is considered that by combination of a structure containing a hydroxyapatite that is a calcium phosphate (hydroxyapatite structure) with living organisms, such as cells and microorganisms, it is possible to produce a biosensor, bioreactor, artificial organ, and the like which use a sensing capability, a material producing capability, and a physiological capability of such living organisms.

Examples of a method for manufacturing such a hydroxyapatite structure include a wet process using the reaction of an aqueous solution, a dry process using solid-phase reaction at a high temperature, a hydrothermal process in which single crystal is grown at a high temperature and at a high pressure, and biomimetic method in which a hydroxyapatite is grown under the conditions close to the conditions of a body's inner environment. Among these methods, especially the biomimetic method is superior in that it can form a hydroxyapatite structure having a large surface area, a high bio-affinity and a high bioactivity.

Non-patent Document 1 specifically discloses a method for obtaining a hydroxyapatite by biomimetic method. Patent Document 1 discloses a method of coating an entire target substance with calcium phosphates by biomimetic method.

As disclosed in these documents, seed crystal as a seed is needed for the growth of calcium phosphates. In these documents, CaO—SiO2 glass powder and a resin film are brought into contact in a simulated body fluid and the resulting solution is let stand for several days, whereby a seed crystal is precipitated on the surface of the film. The thus obtained seed crystal is used as a seed for the growth of calcium phosphates.

[Patent Document 1]
   Japanese Unexamined Patent Publication No. 59001/2005 (Tokukai 2005-59001; Published on Mar. 10, 2005)

[Non-patent Document]
   Masami Tanahashi, et al., J. Am. Ceram. Soc., 77 (11) 2805-808 (1994)

As described previously, a method of precipitating a seed crystal as a seed on the surface of a solid, such as the previously described method using glass powder and a resin film has been carried out to obtain a seed for the growth of calcium phosphates. However, the method using such glass powder raises the problem that it needs a complicated step, including a step of separating the seed crystal from these solids.

An object of the present invention is to provide a method for stabilizing calcium phosphates fine particles, which method was not carried out in the past, and to provide a use of this method, for example, a method for manufacturing calcium phosphates fine particles.

DISCLOSURE OF INVENTION

The inventors of the present invention diligently worked to solve the foregoing problem and accomplished the present invention by finding entirely on their own that it is possible to stabilize calcium phosphates fine particles by stopping the growth of fine particles of calcium phosphates (calcium phosphates fine particles) formed in an aqueous solution which is supersaturated with respect to calcium phosphates, for example, by surrounding calcium phosphates fine particles with a medium with a low inorganic ion concentration. The present invention has been completed on the basis of the above novel findings, and encompasses the following inventions:

(1) A method for stabilizing fine particles of calcium phosphates by stopping growth of the fine particles of calcium phosphates formed in an aqueous solution which is supersaturated with respect to calcium phosphates.

(2) The method as set forth in (1), wherein the growth of the fine particles is stopped by placing the fine particles in an environment of a low inorganic ion concentration.

(3) The method as set forth in (2), wherein the fine particles are placed in the environment of a low inorganic ion concentration by lowering the inorganic ion concentration in the environment where the fine particles are placed.

(4) The method as set forth in (2), wherein the fine particles are placed in the environment of a low inorganic ion concentration by removing inorganic ions from the environment where the fine particles are placed.

(5) The method as set forth in (2), wherein the fine particles are placed in the environment of a low inorganic ion concentration, by at least one operation selected from dialysis, ion exchange, dilution, filtration, and centrifugation.

(6) The method as set forth in (1), wherein the growth of the fine particles is stopped by lowering an inorganic ion concentration of a fine-particle-forming solution containing the fine particles.

(7) The method as set forth in (6), wherein the inorganic ion concentration of the fine-particle-forming solution containing the fine particles is lowered by at least either dialysis or dilution.

(8) The method as set forth in (1), wherein the growth of the fine particles is stopped by separating the fine particles from a fine-particle-forming solution containing the fine particles.

(9) The method as set forth in (8), wherein the fine particles are separated from the fine-particle-forming solution containing the fine particles by at least either filtration or centrifugation.

(10) A method for manufacturing fine particles of calcium phosphates, comprising the method as set forth in any one of (1) through (9) as a step.

(11) Fine particles of calcium phosphates manufactured by the manufacturing method as set forth in (10).

(12) A fine-particle-containing composition containing the fine particles of calcium phosphates as set forth in (11).

(13) A calcium phosphates fine particles-dispersed solution in which the fine particles of calcium phosphates as set forth in (11) are dispersed in water or an organic solvent.

(14) A method for growing calcium phosphates by using the fine particles of calcium phosphates as set forth in (11) as seeds.

(15) A method for manufacturing a calcium-phosphates-containing composition, comprising the method as set forth in (14) as a step.

(16) A calcium-phosphates-containing composition manufactured by the manufacturing method as set forth in (15).

Additional objects, features, and strengths of the present invention will be made clear by the description below. Further, the advantages of the present invention will be evident from the following explanation in reference to the drawings.

BRIEF DESCRIPTION OF DRAWINGS

FIG. 21 is a diagram showing the time-course examination of the generation of calcium phosphates fine particles in 1.5SBFs of pH values in Comparative Example 5 on the basis of Tyndall phenomenon.

BEST MODE FOR CARRYING OUT THE INVENTION

Figure 1:
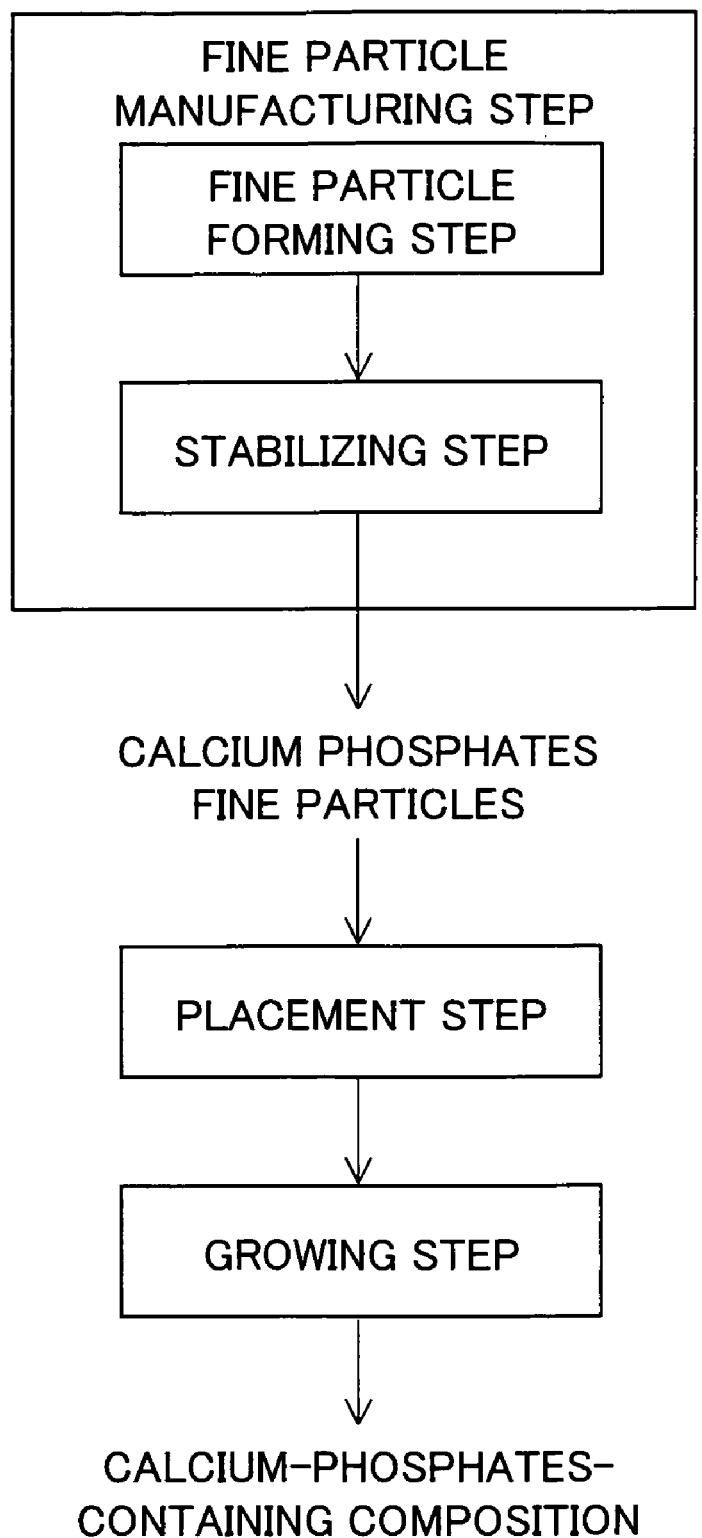
FIG. 1 is a process chart illustrating an embodiment of a method for manufacturing a calcium-phosphates-containing composition according to the present invention.

The present invention relates to a method for stabilizing calcium phosphates fine particles, and use thereof. The following will first describe the method for stabilizing calcium phosphates fine particles, and then describe the use thereof.

<1. Method for Stabilizing Calcium Phosphates Fine Particles>

Conventionally, seeds for the growth of calcium phosphates were obtained by the method of making microcrystal of calcium phosphates precipitated on the surface of a resin film by using a glass or the like, and then separating the microcrystal from the resin film by making the resin film dissolved or ultrasonically vibrating the resin film, to recover the microcrystal that is the seed.

However, the inventors of the present invention diligently worked and found a method for more easily obtaining calcium phosphates fine particles with higher solid phase forming activity and high purity, without undergoing the above conventional steps.

Note that the solid phase forming activity in the present invention is an activity of growing calcium phosphates. In other words, having the solid phase forming activity refers to the capability of functioning as seeds for the growth of calcium phosphates.

A method for stabilizing calcium phosphates fine particles according to the present invention is a method in which an environment where there exist calcium phosphates fine particles formed in an aqueous solution which is supersaturated with respect to calcium phosphates is changed to be an environment with a low inorganic ion concentration so that the growth of the calcium phosphates fine particle is stopped, whereby the calcium phosphates fine particles are stabilized. The arrangements other than this are not particularly limited. That is, steps, reaction conditions, materials, manufacturing devices, manufacturing apparatuses, and others can be suitably the previously known ones, and are not particularly limited. The following will describe in detail.

(Calcium Phosphates)

Examples of calcium phosphates are monocalcium phosphate (Ca(H2PO4)2), dicalcium phosphate (CaHPO4), tricalcium phosphate (Ca3(PO4)2), tetracalcium phosphate (Ca4(PO4)2O), octacalcium phosphate (Ca8H2(PO4)6), apatites including hydroxyapatites, amorphous calcium phosphate, all of which may have crystal water.

(Hydroxyapatites)

A hydroxyapatite is a compound represented by the following formula: Ca10(PO4)6(OH)2. Hydroxyapatites are a hydroxyapatite and a hydroxyapatite whose constituent element(s) is substituted and/or deleted. In hydroxyapatites, for example, part of constituent elements or groups of a hydroxyapatite may be substituted by: such as F or Cl; an element of I group in the periodic table, such as Na or K; an element of II group in the periodic table, such as Mg or Zn; an element of VII group in the periodic table, or a group such as CO32-, HPO42-, or SO42-. Further, part of constituent elements or groups of a hydroxyapatite may be substituted by a rare earth element. Such hydroxyapatites are derived from various elements or groups contained in a solution for forming calcium phosphates (calcium-phosphates-forming solution).

(Calcium Phosphates Fine Particles)

As described previously, the calcium phosphates fine particles of the present invention (which can be hereinafter simply referred to as "fine particles") are the ones that accelerates precipitation of calcium phosphates. More particularly, the calcium phosphates fine particles are fine particles that induce and accelerate the growth of calcium phosphates.

The calcium phosphates fine particles according to the present invention can be any fine particles as long as they contain calcium phosphates and allow calcium phosphates to grow. Note that the calcium phosphates fine particles may contain substance(s) other than calcium phosphates. In other words, the calcium phosphates fine particles according to the present invention can be any fine particles as long as they can function as seeds for the growth of calcium phosphates. Size, form, and others thereof are not particularly limited.

In a case where the fine particles are used in the manufacture of the calcium phosphates, which will be described later, the fine particles can be any fine particles as long as interatomic distance of them is identical with or similar to that of target calcium phosphates, but chemical constitution of them may be different from that of calcium phosphates in a target calcium-phosphates-containing composition.

The size of the calcium phosphates fine particles is in the range from 0.5 nm to 1 mm, preferably 0.6 nm to 100 μm, more preferably 0.7 nm to 10 μm, from the viewpoint of accelerating the growth of calcium phosphates.

The calcium phosphates fine particles can be formed, for example, by preparing an aqueous solution (fine-particle-forming solution described later) which is supersaturated with respect to calcium phosphates, and adjusting pH of the aqueous solution. The method of forming the calcium phosphates fine particles will be described later.

(Method According to the Present Invention)

The inventors of the present invention found that when calcium phosphates fine particles formed in an aqueous solution which is supersaturated with respect to calcium phosphates are placed in an environment with a low inorganic ion concentration, the growth of the calcium phosphates fine particles is stopped, and the calcium phosphates fine particles are stabilized. Note that "stabilizing calcium phosphates fine particles" means keeping calcium phosphates fine particles in a state where they have solid phase forming activity. Therefore, it can be said that "method for stabilizing calcium phosphates fine particles" is a "method for preserving calcium phosphates fine particles for long periods, while keeping the calcium phosphates fine particles in a state where they have solid phase forming activity."

In the presence of inorganic ions, especially hydrogenphosphate ions and/or calcium ions, it is considered that the calcium phosphates fine particles grow, and as a result, solid phase growing activity of the calcium phosphates fine particles is lowered or eliminated. It is be considered that according to the method of the present invention, the calcium phosphates fine particles are placed in an environment with a low inorganic ion concentration to prevent the calcium phosphates fine particles from growing, thus making it possible to stabilize the calcium phosphates fine particles and to preserve them for long periods.

However, this mechanism is merely a hypothesis. The present invention encompasses a mechanism other than the above mechanism if calcium phosphates fine particles are kept in a state where they have solid phase forming activity by placing the calcium phosphates fine particles in an environment with a low inorganic ion concentration.

That is, "stabilizing calcium phosphates fine particles" in the present invention may be maintaining solid phase growing activity of the calcium phosphates fine particles, for example, by stopping the growth of calcium phosphates fine particles.

That is, in the method of the present invention, the environment where calcium phosphates fine particles exist is finally changed to be an environment with such a low inorganic ion concentration that the calcium phosphates fine particles do not grow. A process of changing the environment where calcium phosphates fine particles exist to an environment with a low inorganic ion concentration is not limited.

Note that the environment where the calcium phosphates fine particles are placed, which is not particularly limited, may be a gas, a liquid, or a solid. Further, such an environment may be a vacuum. The environment where the calcium phosphates fine particles are placed can be referred to as "medium". If the calcium phosphates fine particles are dispersed in a gas, a liquid, or a solid, the gas, the liquid, and the solid are media. For convenience of explanation, the present embodiment may regard the placement of calcium phosphates fine particles in a vacuum as the dispersion of calcium phosphates fine particles in a medium.

In the present invention, the method of "placing calcium phosphates fine particles in a low inorganic ion environment" includes a method of lowering an inorganic ion concentration in an environment where the calcium phosphates fine particles are placed.

More specifically, examples of "lowering an inorganic ion concentration in an environment where the calcium phosphates fine particles are placed" include: a method of removing inorganic ions from an environment where the calcium phosphates fine particles are placed; a method of diluting a medium surrounding the calcium phosphates fine particles; and a method of transferring the calcium phosphates fine particles in an environment with a low inorganic ion concentration.

Examples of the method of removing inorganic ions from an environment where the calcium phosphates fine particles are placed include removing at least part of inorganic ions by dialysis, multiple dialysis and/or ion-exchange resin, or others.

Further, diluting a medium surrounding the calcium phosphates fine particles may be specifically lowering an inorganic ion concentration by adding distilled water or the like into a solution containing the calcium phosphates fine particles.

Still further, transferring the calcium phosphates fine particles in an environment with a low inorganic ion concentration may be specifically substituting a medium surrounding the calcium phosphates fine particles by a medium whose inorganic ion concentration is lower than the original medium. Examples of the method of transferring the calcium phosphates fine particles in an environment with a low inorganic ion concentration include the following methods. First, calcium phosphates fine particles are separated by filtration, centrifugation, or the like from a first medium surrounding the calcium phosphates fine particles. Such a separation can be the substitution of the medium surrounding the calcium phosphates fine particles by a second medium with a low inorganic ion concentration, i.e. an air. The thus separated calcium phosphates fine particles may be preserved in an air as they are, or may be mixed with another medium such as a liquid. Further, placing the calcium phosphates fine particles in a vacuum may be placing the calcium phosphates fine particles in a low inorganic ion environment with a low inorganic ion concentration.

More specifically, the calcium phosphates fine particles may be fine particles formed in a fine-particle-forming solution, which will be described later. In this case, it is possible to stabilize the calcium phosphates fine particles by lowering an inorganic ion concentration of the fine-particle-forming solution containing the calcium phosphates fine particles. This may be, for example, the following methods: a method of removing at least part of inorganic ions by dialysis, multiple dialysis and/or ion-exchange resin, or others; and a method of lowering an inorganic ion concentration by adding distilled water or the like into a solution containing the calcium phosphates fine particles.

Furthermore, it is possible to stabilize the calcium phosphates fine particles by separating the calcium phosphates fine particles from the fine-particle-forming solution containing the calcium phosphates fine particles. The thus separated calcium phosphates fine particles may be preserved in an air as they are or may be mixed with other medium such as a liquid. Examples of the separation include filtration and centrifugation.

Note that in a case where inorganic ions are removed by dialysis from a medium surrounding fine particles, a dialysis tube as used can be appropriately changed according to a size of fine particles to be desired. That is, if smaller fine particles are to be desired, a dialysis tube having a low molecular weight cut off is used. On the other hand, if larger particles are to be desired, a dialysis tube having a high molecular weight cut off is used. Although the dialysis tube has preferably a high molecular weight cut off from the viewpoint of lowering an inorganic ion concentration as quickly as possible, the dialysis tube can be set appropriately in consideration of the existence of the fine particles passing through the dialysis tube to the outside.

Furthermore, the low inorganic ion concentration, which is not particularly limited, can be any state in which calcium phosphates fine particles are stably maintained. That is, type, concentration, and others of inorganic ions in the environment where the calcium phosphates fine particles are placed may be any type, any concentration, and others as long as they do not lower the solid phase growing activity of the calcium phosphates fine particles. Examples of inorganic ions that especially preferably exist with low concentrations include hydrogenphosphate ions and calcium ions. Specifically, for example, in a case where the calcium phosphates fine particles are stabilized with an aqueous solution, low inorganic ion concentration is "a concentration of hydrogenphosphate ions and calcium ions which concentration is not higher than a solubility product of calcium phosphates."

Even in the case of other inorganic ions, the concentration of ions which lower the solid phase forming activity of the calcium phosphates fine particles is preferably set to be low. Further, although the concentration of such inorganic ions is preferably set to be lower, the concentration is not particularly limited as long as it is a concentration which enables the solid phase forming activity of the calcium phosphates fine particles to be maintained. In addition to these ions, all inorganic ions preferably have as low a concentration as possible. However, ions which do not grow the calcium phosphates fine particles and do not lower the solid phase forming activity thereof may be present in a medium surrounding the calcium phosphates fine particles.

Note that in the present invention, the hydrogenphosphate ion is a generic name for a phosphoric acid capable of producing $PO_4^{3-}$ in an aqueous solution. That is, in the present invention, a phosphoric acid ($H_3PO_4$), dihydrogenphosphate ion ($H_2PO_4^-$), hydrogenphosphate ion ($HPO_4^{2-}$), and phosphate ion ($PO_4^{3-}$) are generically called hydrogenphosphate ion. The hydrogenphosphate ion also includes a condensed phosphoric acid produced by polymerization of two or more PO4 tetraherons.

The calcium phosphates fine particles stabilized by the method of the present invention can be preserved for long periods while retaining a high solid phase forming activity. As will be described later, such calcium phosphates fine particles are useful per se, can be used for a fine-particle-containing composition, and further can be suitably in the manufacture of a calcium-phosphates-containing composition.

Other arrangements and more specific arrangements of the method of the present invention will be described in (Stabilizing step) in section <2> below.

As described above, a method for stabilizing calcium phosphates fine particles according to the present invention enables calcium phosphates fine particles to be preserved for long periods without lowing solid phase forming activity of the calcium phosphates fine particles. This method can be used suitably as a step of a method for manufacturing calcium phosphates fine particles, which will be described later. Unlike the conventional manufacturing method, the manufacturing method of the present invention eliminates the need for addition of an insoluble material such as glass powder, and thus enables calcium phosphates fine particles with high bio-affinity and high solid phase forming activity to be easily manufactured in large quantity. The method for manufacturing calcium phosphates fine particles will be described later.

The calcium phosphates fine particles stabilized by the method of the present invention can be preserved or used as they are, or dispersed in a parent material capable of keeping the calcium phosphates fine particles in a stable manner, so as to make up a fine-particle-containing composition. The parent material and fine-particle-containing composition used in this case will be described later.

<2. Method for Manufacturing Calcium Phosphates Fine Particles>

The method for manufacturing calcium phosphates fine particles of the present invention includes the method for stabilizing calcium phosphates fine particles, which has been described in section <1> above, as a step (stabilizing step).

The following will describe, as an example of such a manufacturing method, a manufacturing method in which the stabilizing step includes a fine particle forming step of forming calcium phosphates fine particles from a fine-particle-forming solution.

As illustrated in FIG. 1, the method for manufacturing calcium phosphates fine particles according to the present embodiment includes the fine particle forming step of manufacturing calcium phosphates fine particles and the stabilizing step of stabilizing the calcium phosphates fine particles.

(Fine Particle Forming Step)

In the fine particle forming step, a fine-particle-forming solution is prepared and optionally subjected to a further treatment such as ultrasonic treatment, so that the calcium phosphates fine particles described in section <1> above are formed.

The fine-particle-forming solution is an aqueous solution capable of forming the calcium phosphates fine particles described in section <1> above, i.e. an aqueous solution containing calcium ions (Ca2+) and hydrogenphosphate ions. Other constituents and concentrations of solutes, and others are not particularly limited.

In order to form calcium phosphates fine particles, it is important to appropriately adjust the concentrations of ions in a solution, especially concentrations of calcium ions (Ca2+) and hydrogenphosphate ions, and to appropriately adjust pH thereof. If the pH is high (more basic), calcium phosphates fine particles in a solution become large in size, and are therefore likely to coagulate and precipitate. On the other hand, if the pH is low (more acidic), the fine particles become small in size. If the pH is much lower, no fine particles are formed. In this manner, the degree of the pH determines the generation of the fine particles and size thereof. That is, the fine particle forming step may include a step of adjusting pH of the fine-particle-forming solution.

Specifically, the fine-particle-forming solution preferably contains 0.02 mM to 25 mM of calcium ions and 0.01 mM to 10 mM of hydrogenphosphate ions and has pH 4 to 9. More preferably, the fine-particle-forming solution contains 0.2 mM to 20 mM of calcium ions and 0.1 mM to 8 mM of hydrogenphosphate ions, and has pH 6.2 to 8.0. Further preferably, the fine-particle-forming solution contains 1.2 mM to 5 mM of calcium ions and 0.5 mM to 2 mM of hydrogenphosphate ions, and has pH 7.2 to 7.9. Especially preferably, the pH is adjusted to be approximately in a range from 7.4 to 7.8.

A calcium-phosphates forming solution is preferably prepared by using dibasic potassium phosphate trihydrate and calcium chloride. The pH of the calcium-phosphates forming solution is preferably adjusted by using a proper buffer solution, e.g. NH2C(CH2OH)3, and further by addition of an acid such as hydrochloric acid.

In order to form calcium phosphates fine particles with excellent biocompatibility, it is preferably to use the so-called simulated body fluid (SBF) which is a solution containing, for example, sodium chloride, sodium hydrogen carbonate, potassium chloride, magnesium chloride hexahydrate, and sodium sulfate, as well as calcium ions and hydrogenphosphate ions, and whose composition is similar in inorganic ion concentration to blood plasma of a human. The SBF prepared may contain 1.4 mM to 1420 mM of sodium ions (Na+), 0.05 mM to 50 mM of potassium ions (K+), 0.01 mM to 15 mM of magnesium ions (Mg2+), 1.4 mM to 1500 mM of chloride ions (Cl—), 0.04 mM to 45 mM of hydrogen carbonate ions (HCO3-), and 5.0×10−3 mM to 5 mM of sulfate ions (SO42-). Preferably, the SBF prepared may contain 14 mM to 1140 mM of sodium ions, 0.5 mM to 40 mM of potassium ions, 0.1 mM to 12 mM of magnesium ions, 14.5 mM to 1200 mM of chloride ions, 0.4 mM to 36 mM of hydrogen carbonate ions, and 0.05 mM to 4 mM of sulfate ions. More preferably, the SBF prepared may contain 70 mM to 290 mM of sodium ions, 2.5 mM to 10 mM of potassium ions, 0.7 mM to 3.0 mM of magnesium ions, 70 mM to 300 mM of chloride ions, 2.0 mM to 9.0 mM of hydrogen carbonate ions, and 0.2 mM to 1.0 mM of sulfate ions.

Especially, an SBF whose inorganic ion concentration is close to that of a body fluid is referred to as 1.0SBF. The 1.0SBF contains the composition of inorganic components as follows: 142.0 mM of sodium ions, 5.0 mM of potassium ions, 1.5 mM of magnesium ions, 2.5 mM of calcium ions, 148.8 mM of chloride ions, 4.2 mM of hydrogen carbonate ions, 1.0 mM of hydrogenphosphate ions, and 0.5 mM of sulfate ions.

The fine-particle-forming solution can form fine particles without being subjected to other special treatment, as long as the solution is prepared to be supersaturated with respect to a calcium phosphate. Note that the expression "being supersaturated" in the present invention is a state which takes into consideration the influence of pH. That is, even at the same concentration and the same temperature, the solubility of calcium phosphates in a solvent varies depending upon a pH. The expression "being supersaturated" herein does not define only the concentration of a solvent, but indicates that the conditions including pH are sufficient to form the calcium phosphates fine particles.

However, in a case where the solution is not supersaturated, i.e. in a case where the solution is not supersaturated due to conditions including concentration of a solvent and/or pH, in a case where no calcium phosphates fine particles are formed even though the solution is supersaturated, it is possible to form the fine particles by a treatment to accelerate the formation of the fine particles, such as addition of a precipitation-inducing substance and/or ultrasonication. Details of these techniques will be described below.

The precipitation-inducing substance is a substance that induces precipitation of calcium phosphates. Examples of such a precipitation-inducing substance preferably are calcium phosphates, a glass of particular composition and/or a crystallized glass, such as CaO—SiO2 glass, phosphate glass, Na2O—CaO—SiO2-P2O5 glass, Na2O—K2O—MgO—CaO—SiO2-P2O5-CaF2 glass, or MgO—CaO—SiO2-P2O5-CaF2 crystallized glass, or wollastonite. The precipitation-inducing substance can also be a substance having a Si—OH group, a Zr—OH group, a Ti—OH group, a Ta—OH group, a PO3 group, a COOH group, or the like on its surface.

Furthermore, ultrasonic waves can accelerate the formation of the fine particles. For example, when a fine-particle-forming solution of which pH is low to such an extent that no fine particles are formed is subjected to ultrasonication, the fine particles can be formed.

In addition, ultrasonic waves have the effect of dispersing calcium phosphates fine particles. Through the use of this effect, coagulation of calcium phosphates fine particles is prevented by ultrasonic waves. Thus, it is possible to manufacture calcium phosphates fine particles with a high solid phase forming activity.

Also, by subjecting the fine-particle-forming solution supersaturated with respect to calcium phosphate to pH adjustment, and ultrasonication, and others, it is possible to accelerate the formation of the fine particles and adjust the diameter of the fine particles, and others.

(Stabilizing Step)

The stabilizing step is a step of stabilizing calcium phosphates fine particles. As this step, the method for stabilizing calcium phosphates fine particles, which has been described in section <1> above, can be adopted.

In the manufacturing method according to the present embodiment, the stabilizing step is a step of stabilizing the calcium phosphates fine particles formed in the foregoing fine particle forming step. However, the present invention is not limited to this.

The stabilizing step and the fine particle forming step, which are not necessarily performed separately, may be performed simultaneously (in parallel with each other). The adjustment of a fine particle diameter through pH adjustment, the addition of a precipitation-inducing substance, and the ultrasonication, all of which have been described in subsection (Fine particle forming step), can be also adopted in the stabilizing step.

Specifically, the pH of the fine-particle-forming solution used in the stabilizing step is changed according to a size of target calcium phosphates fine particles. The pH is lowered to obtain smaller calcium phosphates fine particles, and the pH is raised to obtain larger calcium phosphates fine particles.

The stabilizing step may be performed in a state where the precipitation-inducing substance is added to the fine-particle-forming solution, so as to accelerate the formation of the calcium phosphates fine particles. In addition, ultrasonication may be performed during the stabilizing step, so as to accelerate the formation of the calcium phosphates fine particles and disperse the fine particles.

The stabilizing step is preferably performed right after (or simultaneously with) the fine particle forming step. That is, it is preferable that the calcium phosphates fine particles are placed in an environment with low inorganic ion concentration in the shortest possible time after they are formed. This makes it possible to obtain fine particles with especially high solid phase forming activity. If the fine particles are left in an environment with high inorganic ion concentration (e.g. in the fine-particle-forming solution), the fine particles grow. As a result, the solid phase forming activity thereof is lowered. Note that the high inorganic ion concentration herein refers to especially a state where the concentrations of hydrogenphosphate ions and calcium ions are high.

The fine particles stabilized by undergoing the stabilizing step are processed into an intended form, through further step(s) if necessary.

As compared with the conventional method using glass powder, the method for manufacturing calcium phosphates fine particles of the present invention enables the process to be simplified, and enables the calcium phosphates fine particles with high solid phase forming activity to be manufactured in large quantity through easy operation. For example, only by dialysis of the simulated body fluid, it is possible to manufacture the calcium phosphates fine particles. Further, even in a case where the contamination of glass powder is not preferable, it is possible to obtain the calcium phosphates fine particles through the manufacturing method of the present invention.

(Fine-Particle-Containing Composition)

In the present invention, the fine-particle-containing composition is a substance containing the calcium phosphates fine particles manufactured by the foregoing method. Other constituents and the amounts of calcium phosphates fine particles contained, a manner in which the calcium phosphates fine particles are contained (mixture, dispersion, etc.), and other conditions are not particularly limited.

The fine-particle-containing composition may be a parent material in which calcium phosphates fine particles were dispersed, i.e. the fine-particle-containing composition may be a product including substances being dispersed. The parent material used in this case may be appropriately changed according to an intended use of the fine-particle-containing composition, and others.

The parent material as used may be a gas, a liquid, or a solid. For example, if the parent material as used is a liquid, it may be an aqueous solution or an organic solvent. More specifically, the parent material can be ketone such as acetone, alcohol such as ethanol and methanol, ether, kerosene, or the like. A calcium phosphates fine particles-dispersed solution in which calcium phosphates fine particles are dispersed in water or the organic solvent exemplified above is extremely useful as a preservation solution for preserving the calcium phosphates fine particles with high solid phase forming activity for long periods.

Further, it is preferable that the solid includes rubber, plastic, metal, ceramic, and glass, and is a substance that can turn to a liquid according to a temperature and/or other conditions, and can have the fine particles dispersed therein. The parent material may be the one solidified with elasticity and solidity in the form of a jelly, as typified by gel. Further, the parent material can be an aerosol in which fine particles are dispersed in a gas. The parent material as used may be changed appropriately according to an intended use of the fine-particle-containing composition, and others.

Furthermore, the parent material can be used as a medium of low inorganic ion concentration, surrounding the calcium phosphates fine particles in the method for stabilizing the calcium phosphates fine particles, which method has been described in section <1>. That is, in the above method (i.e. stabilizing step), it is possible to stabilize the calcium phosphates fine particles by dispersing the calcium phosphates fine particles in such a parent material. In other words, it is possible to manufacture the fine-particle-containing composition through the stabilizing step.

Examples of the fine-particle-containing composition include the foregoing fine-particle-forming solution obtained by the stabilizing step, such as dialysis or dilution.

In a case where the parent material is a liquid, it is possible to adjust the concentration of the calcium phosphates fine particles by removing the liquid by evaporation and/or filtration, or other operation, or to take out the fine particles by removing the parent material.

The calcium phosphates fine particles according to the present invention have high solid phase forming activity, and are therefore used suitably in the growth of calcium phosphates and the manufacture of a calcium-phosphates-containing composition, both of which will be described later.

Further, the calcium phosphates fine particles according to the present invention can form an osteoid calcium phosphate layer on their surface in a living body, and bind to a bone of a living body without any fibrous tissue therebetween. That is, the calcium phosphates fine particles according to the present invention have a bioactivity. Still further, the calcium phosphates fine particles according to the present invention have a high bio-affinity.

Thus, the calcium phosphates fine particles and fine-particle-containing composition according to the present invention can be used suitably in medical treatments especially for tooth-related and bone-related disorders and diseases. Specifically, the fine-particle-containing composition (e.g. gelled composition) is made deposited on a tooth or a bone. At the location where the fine-particle-containing composition is deposited, calcium phosphates grow. This makes it possible to regenerate a tooth or a bone. The fine-particle-containing composition of the present invention encompasses various kinds of industrial products containing the calcium phosphates fine particles, such as medical products and toothpastes containing the calcium phosphates fine particles.

<3. Method for Growing Calcium Phosphates>

The method for growing the calcium phosphate according to the present invention is a method for growing calcium phosphates around the calcium phosphates fine particles, which are manufactured by the manufacturing method described in section <2> above, as the seeds. Other steps, etc. are not limited.

In order to grow the calcium phosphates, the conventional calcium phosphates growing method can be suitably used. That is, any of a wet process, a dry process using solid-phase reaction at a high temperature, a hydrothermal process in which single crystal is grown at a high temperature and at a high pressure, biomimetic method, or the like can be used.

In order to grow the calcium phosphates, the calcium-phosphates-growing solution, which will be described later, is brought into contact with the calcium phosphates fine particles. With this arrangement, the calcium phosphates grow while the calcium phosphates fine particles serve as the seeds.

The calcium-phosphates-growing solution can be a solution whose composition is similar to that of the fine-particle-forming solution, which has been described in section <2>. Apart from this, a solution containing hydrogenphosphate ions and calcium ions can be used.

In this calcium-phosphates-growing solution, organic polymer may be dissolved. Examples of the organic polymer include collagen, chitin, polylactic acid, polyethylene, polyethylene terephthalate, polymethyl methacrylate, polypropylene, polystyrene, and silicone. Especially, collagen, chitin, and other biopolymer are preferably used. For example, in a case where collagen is used, the calcium phosphates grown by the method of the present invention, i.e. the later described calcium-phosphates-containing composition is used suitably for an artificial bone material.

The concentrations of sodium ions, chloride ions, or other coexistent ions in the calcium-phosphates-growing solution have influence on a growth rate of the calcium phosphates, and therefore should be adjusted appropriately according to purposes. In addition to the concentrations, the change of pH and temperature and others can adjust the growth rate. At a low growth rate, close-grained calcium phosphates grow.

A method of bringing the calcium-phosphates-growing solution into contact with the calcium phosphates fine particles is not particularly limited. For example, the calcium phosphates fine particles or a base material on which the calcium phosphates fine particles are deposited may be immersed in the calcium-phosphates-growing solution, or the calcium-phosphates-growing solution may be sprayed onto the calcium phosphates fine particles or a base material on which the calcium phosphates fine particles are deposited. More specific methods will be described in section <4> below.

The method for growing the calcium phosphates is particularly preferably a biomimetic method. The biomimetic method is a method for growing calcium phosphates under the conditions close to those in a body's internal environment. The conditions close to those in a body's internal environment refers to conditions where the foregoing simulated body fluid is used and a temperature is in a body temperature range, i.e. approximately in the range from 36° C. to 37° C. However, the present invention is not limited to this. In the method for growing the calcium phosphates according to the present invention, it is particularly preferable to use a simulated body fluid, but a temperature adopted is not particularly limited.

The calcium phosphates grown by the biomimetic method are called biological apatite, and have characteristics that part of a phosphate group is substituted by carbonate ions, and other characteristics. Therefore, the biomimetic method, which allows for the formation of calcium phosphates with a high bio-affinity and a high bioactivity, is suitably adopted in a method for manufacturing a calcium-phosphates-containing composition to be used in a living body. The following will mainly describe a method for growing calcium phosphates by the biomimetic method. However, as a matter of course, the present invention is not limited to this.

<4. Calcium-Phosphates-Containing Composition and Method for Manufacturing the Same>

(Manufacturing Method)

The method for manufacturing a calcium-phosphates-containing composition according to the present invention have only to include the method described in section <3> above as a step (growing step). Other steps, etc. are not particularly limited. Details of the calcium-phosphates-containing composition will be described later.

An example of the manufacturing method of the present invention will be described below with reference to FIG. 1. FIG. 1 is a process chart illustrating the method for manufacturing a calcium-phosphates-containing composition according to the present embodiment.

As illustrated in FIG. 1, the manufacturing method according to the present embodiment includes: an placement step of placing calcium phosphates fine particles at an intended location; and a growing step of growing calcium phosphate around the calcium phosphates fine particles that have undergone the placement step. Note that although the step of manufacturing calcium phosphates fine particles (the fine particle manufacturing step) is shown in FIG. 1, an explanation of the manufacturing step is omitted herein because the fine particle manufacturing method described in section <2> above can be applied to this step.

(Placement Step)

The placement step of the present embodiment has only to be a step of placing calcium phosphates fine particles at an intended location, and how to place the fine particles at the intended location is not limited.

Note that the placement at the intended location include the deposition of calcium phosphates fine particles on a base material, and assembly of calcium phosphates fine particles by themselves without the use of a base material or the like.

Hardness, form, composition, size, etc. of the base material is not particularly limited. The base material can be any of various kinds of substances including gel, metal, ceramic, protein, and DNA.

As to some base materials, the calcium phosphates fine particles are less likely to be deposited on their surfaces. In such a case, the base materials should be subjected to surface treatment typified by surface modification, such as plasma, ablation, exposure to ultraviolet rays, and/or graft polymerization.

The base material may be contained in the completed calcium-phosphates-containing composition, or may be removed after the placement step or the growing step.

The calcium phosphates fine particles can be placed, for example, by deposition, adsorption, placement on a phase-to-phase interface, spraying, application, dielectrophoresis, electrophoresis, chromatography, centrifugal force, and/or magnetic force.

As to the placement on the phase-to-phase interface, a phase-to-phase interface is a liquid-to-liquid interface, a solid-to-liquid interface, a gas-to-solid interface, a gas-to-liquid interface, or other combinations, but is not particularly limited. The placement on the solid-to-liquid interface is made by immersion, for example. The immersion is a process of immersing the base material into a solution in which the calcium phosphates fine particles are dispersed, whereby the calcium phosphates fine particles are deposited on the surface of the base material. The placement on the solid-to-solid interface is made by bringing a gel containing the calcium phosphates fine particles into contact with the base material. In this manner, the calcium fine particles are placed on the surface of the base material. Further, the calcium phosphates fine particles dispersed in a gas are brought into contact with the base material, whereby the calcium phosphates fine particles are assembled on the surface of the base material (gas-to-solid interface). In a method without using a solid (base material), i.e. a method using a liquid-to-liquid interface, a gas-to-liquid interface, and the like interface, the calcium phosphates fine particles can be assembled by themselves without using the base material.

As a spraying method, by spraying a dispersed solution onto the base material through ink-jetting or the like, it is possible to place the calcium phosphates fine particles at the intended location. Further, by applying a liquid in which the calcium phosphates fine particles are dispersed onto the base material, it is possible to place the calcium phosphates fine particles on the base material.

By dielectrophoresis, it is possible to place the calcium phosphates fine particles at the intended location, without using the base material.

Further, by using any of these methods described previously, a pattern can be formed. In this case, for example, a pattern may be formed with a resist on the surface of the base material. Then, the calcium phosphates fine particles are deposited on the base material by immersion or other operation. Thereafter, the resist is dissolved with an organic solvent so that the calcium phosphates fine particles formed on the resist are removed. In this manner, a pattern of the calcium phosphates fine particles is formed on the surface of the base material. Thus, the base material on which the calcium phosphates fine particles are deposited is subjected to the growing step, which will be described later. This makes it possible to form a desired pattern of calcium phosphates on the surface of the base material. After the later-described growing step, excess calcium phosphates formed on the resist may be removed. However, it is preferable to remove the extra calcium phosphates before the growing step, since it is possible to form a more accurate pattern.

In the placement step, in a case where the calcium phosphates fine particles are dispersed in a slow-drying organic solvent that is less likely to evaporate and then used, for example, in a case where the base material is immersed in a slow-drying organic solvent in which the calcium phosphates fine particles are dispersed, the base material having undergone the placement step is washed with a quick-drying organic solvent, so that the slow-drying organic solvent can be removed.

In the placement step, in a case where the calcium phosphates fine particles are dispersed in a liquid and then used (e.g. applied onto the base material), the liquid may be a substance that forms a coating when dried. It is possible to expose the calcium phosphates fine particles at the surface of the coating by dissolving the surface of the coating with a solvent.

(Growing Step)

For the growing step in the manufacturing method of the present invention, the "method for growing calcium phosphates" described in section <3> above can be used suitably. That is, the growing step is a step of growing calcium phosphates around the seeds that are made up of calcium phosphates fine particles placed at the intended location in the placement step.

As described in section <3> above, in order to grow the calcium phosphates, the calcium-phosphates-growing solution has only to be brought into contact with the calcium phosphates fine particles placed. In this case, since a substance containing the calcium-phosphates-growing solution is used to contact with the fine particles, a liquid, a gel, or the like which contains the growing solution is used.

A method of bringing the calcium-phosphates-growing solution into contact with the fine particles is as follows. In a case where calcium phosphates fine particles are placed on the base material in the placement step, the base material with the particles is immersed in the calcium-phosphates-growing solution. In a case where ink-jetting is used in the placement step, the calcium-phosphates-growing solution may be supplied by ink-jetting simultaneously with or after the supply of the calcium phosphates fine particles.

(Calcium-Phosphates-Containing Composition)

The calcium-phosphates-containing composition of the present invention may be anything as long as it contains the calcium phosphates manufactured by the foregoing manufacturing method. Other constituents, the amount of calcium phosphates contained, etc. are not particularly limited.

The calcium phosphates have excellent bio-affinity and bioactivity. For this reason, the calcium-phosphates-containing composition according to the present invention is particularly suitable for the use in the medical field. With the use of the calcium-phosphates-growing solution in the foregoing growing step, it is possible to obtain a calcium-phosphates-containing composition that is close to chemical composition in a living body and has particularly excellent bio-affinity and bioactivity.

Note that the calcium-phosphates-containing composition of the present invention also includes a calcium phosphates structure (a structure made up of calcium phosphates or a structure made up of calcium phosphates and other substance), and a complex of the calcium phosphates structure and other substance (target substance) (calcium phosphates complex).

Specifically, the calcium-phosphates-containing composition according to the present invention includes: (i) medical products such as a therapeutic agent, a test agent, an artificial bone, an artificial tooth, an artificial joint, transdermal terminal, an artificial soft tissue, and a chip device; (ii) various kinds of industrial products including cosmetics, a pattern, and a micromachine, and (iii) materials of these products. The calcium-phosphates-containing composition according to the present invention also includes medical devices, such as a biosensor, a bioreactor, and an artificial organ, which use a sensing capability, a material producing capability, and a physiological capability of the living organisms, such as a cell and a microorganism, held in the calcium phosphates structure. Further, the calcium-phosphates-containing composition according to the present invention is applicable to a drug delivery system, an electronic device, an optical device, a magnetic material, a biodevice, a filling material of chromatogram, and an adsorbent of an organic substance and a living organism.

Still further, the calcium-phosphates-containing composition according to the present invention, which can pass through a cell membrane and be dissolved inside a cell, can be used for the purpose of introducing the target object into a cell.

Yet further, the calcium-phosphates-containing composition according to the present invention is also used for foods, or for architectural purposes, including the purpose of preventing damage to concretes.

If the calcium-phosphates-containing composition according to the present invention is a complex with other substance (target substance), the target substance is a medical agent (e.g. antitumor agent, anticancer agent), a radioactive substance, an antibody, an antioxidant, a magnetic material for therapeutic purpose, osteogenic accelerator, a protein, a nucleic acid (DNA, RNA), an enzyme, a nutrient, a magnetic material, a metal, a semiconductor, a glass, a ceramic, a carbon material (e.g. amorphous carbon), a diamond, a salt such as plaster and the like, an organic polymer, a natural product, a poisonous substance, a deleterious substance, a cell, a microorganism, etc. Further, the target substance includes artificial objects such as a micromachine, and a chip device. The calcium phosphates complex containing these target substances is placed at a given location (e.g. affected part that needs medical treatment), thereby exerting the capabilities of the target substances. The calcium-phosphates-containing composition of the present invention stably remains especially on a bone.

For the applications of the calcium-phosphates-containing composition of the present invention to foods, a complex may be formed with a food additive, such as an oxidation inhibitor (vitamin C, vitamin E, sesame oil, etc.), an antibacterial agent (silver, tannin, ginger extract, etc.), and an antiseptic agent.

Alternatively, a complex formed with an alkaline agent, a fungicide, a bactericide, or the like, is kneaded with a concrete material to release the above substance therein. This makes it possible to prevent neutralization, rust of a reinforcing iron bar, deterioration caused by sulfur-oxidizing bacteria, fungi, or the like and to extend life of a structure of concrete.

As to the calcium phosphates complex, the target substance may be coated in whole or in part with the calcium phosphates structure, according to purposes. For example, in a case where the medical agent or the like is coated in whole with the calcium phosphate structure, i.e. in the case of a calcium phosphates complex in which the target substance is encapsulated, the medical agent (encapsulated object) can be gradually released at an affected part that needs medical treatment. Thus, it is possible to exert the effect of the medical agent for long periods. Similarly, the calcium phosphates complex in which a food additive such as an antiseptic agent is encapsulated gradually releases the encapsulated substance in a food for long periods, and exerts the effect of preventing deterioration of a food for long periods.

More specifically, many of the calcium phosphates made by the biomimetic method have pores. Through the pores, the medical agent or the like is released. If there are no pores in the calcium phosphates, the medical agent or the like is released while the calcium phosphates are gradually dissolved inside a body.

In the case where the calcium-phosphates-containing composition is a complex of the calcium phosphates structure and a radioactive substance, calcium phosphates do not need to dissolve. In this case, the calcium phosphates are directly connected to a bone and stably stay at an affected part, thereby irradiating the affected part with radioactive rays.

Note that the target substance may be identical with the base material used in the foregoing placement step and growing step. That is, a complex of the target substance and calcium phosphates may be formed in the growing step. Further, a structure containing the calcium phosphates grown in the growing step may be combined with the target substance separately.

The present invention is not limited to the aforementioned embodiments and is susceptible of various changes within the scope of the accompanying claims. Also, an embodiment obtained by suitable combinations of technical means disclosed in the different embodiments are also included within the technical scope of the present invention.

EXAMPLES

The following Examples describe details of the present invention. However, the present invention is not limited to this. Calcium phosphates including hydroxyapatites are formed in the present Examples. Hereinafter, calcium phosphates formed in the present Examples are simply referred to as hydroxyapatites.

In the following Examples and Comparative Examples, the expressions "1.0SBF adjusted to be pH . . . ", "1.0SBF was adjusted to be pH . . . ", "1.0SBF (pH . . . )", and the like, are expressions indicating "a solution in which a prepared 1.0SBF (pH7.4) was adjusted to be pH . . . " for convenience. As to 1.5SBF and 0.5SBF, similar expressions are also used.

Example 1

(A) Preparation of 1.5SBF 1.5SBF is a calcium-phosphates-forming solution whose inorganic ion concentration is 1.5 times that of 1.0SBF (simulated body fluid) described below. Note that in Example 1, the 1.5SBF was used as a fine-particle-forming solution and a calcium-phosphates-growing solution.

In 700 mL of distilled water were dissolved 11.999 g of NaCl, 0.525 g of NaHCO3, 0.336 g of KCl, 0.342 g of K2HPO4.3H2O, 0.458 g of MgCl2.6H2O, 52.5 ml of 1M hydrochloric acid, 0.417 g of CaCl2, 0.107 g of Na2SO4, 9.086 g of tris(hydroxymethyl)aminomethane. The resulting solution was adjusted with 1M hydrochloric acid to be pH 7.4 at 36.5° C., in order to prepare 1.5SBF whose total volume became 1 L.

(B) pH Adjustment

Tris(hydroxymethyl)aminomethane was added to 1.5SBF so that pH of the resulting solution was increased up to 8.3. The solution became whitely turbid.

By using hydrochloric acid, the pH of the solution was decreased to 7.8. Approximately pH 7.8 is a point at which the solution becomes limpid without white turbidity. Note that dialysis of the solution at pH 8.3 is not preferable because hydroxyapatites generated in the solution during the dialysis aggregate and precipitate. In Example 1, a combination of the preparation of 1.5SBF (step in section (A) above) and the pH adjustment is regarded as a fine particle forming step.

(C) Stabilizing Step

In the present Example, the inorganic ion concentration of the 1.5SBF was decreased by dialysis as the stabilizing step. Specifically, the solution in section (B) above was used as a fine-particle-forming solution, and the following operation was performed at room temperature (25° C.).

The solution in section (B) above was overfilled in a dialysis tube (RC dialysis tube: pore 6, regenerated cellulose film, manufactured by Spectrum) having a molecular weight cut off of 1000, and one end of the dialysis tube was secured with a weighted closer, and the other end was secured with a closer with no weight. The dialysis tube was allowed to stand upright in a reservoir containing 2000 ml of distilled water. The distilled water in the reservoir was slowly stirred with a stirrer. The distilled water in the reservoir was replaced by fresh distilled water 1 hour later, 3 hours later, 7 hours later, 15 hours later, and 39 hours later. After a lapse of further 48 hours, the dialysis was completed. The resulting dialysis internal solution is a solution in which stabilized calcium phosphates fine particles are dispersed.

A few milliliters of the dispersed solution was taken out, silver nitrate aqueous solution was dropped off into the thus taken dispersed solution, and it was observed that white turbidity (precipitation of silver chloride) appeared a little. This proved that various kinds of inorganic ions contained in the 1.5SBF were lost by dialysis, and the inorganic ion concentration of the 1.5SBF became low. The original 1.5SBF contains a large amount of chloride ions. However, chloride ions were lost by dialysis at this moment, and the concentration of other inorganic ions was also low (low inorganic ion concentration) at the same time.

(D) Placement Step 30 ml of the dispersed solution in section (C) above was put into polystyrene bin. PESF (polyethersulfone, base material) was immersed in this dispersed solution at 36.5° C. for 24 hours, while being hung with a clip. Note that the temperature is not limited to 36.5° C.

(E) Growing Step

Figure 2:
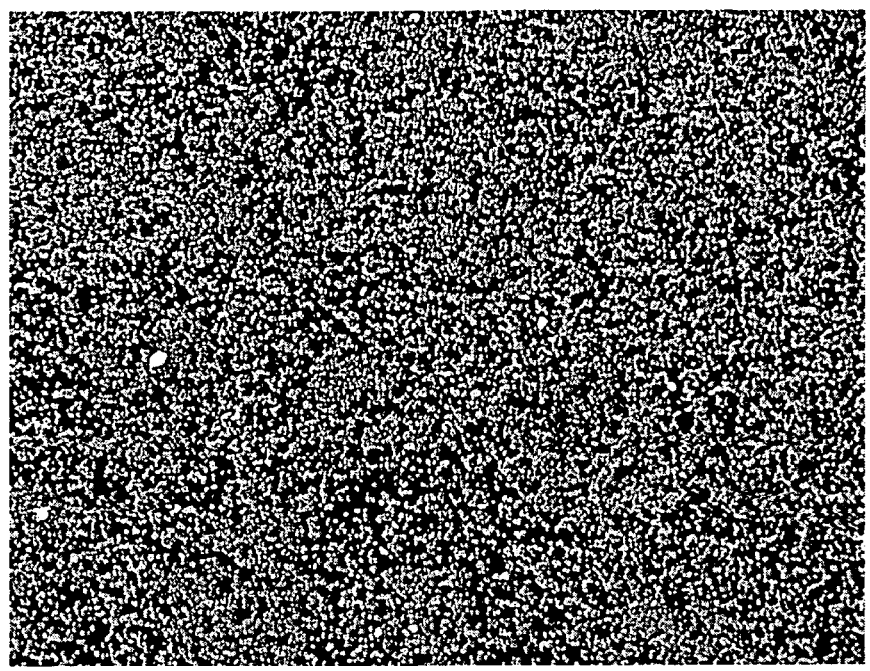
FIG. 2 is a scanning electron micrograph showing the external structure of a calcium phosphates structure according to Example 1 of the present invention.
Figure 3:
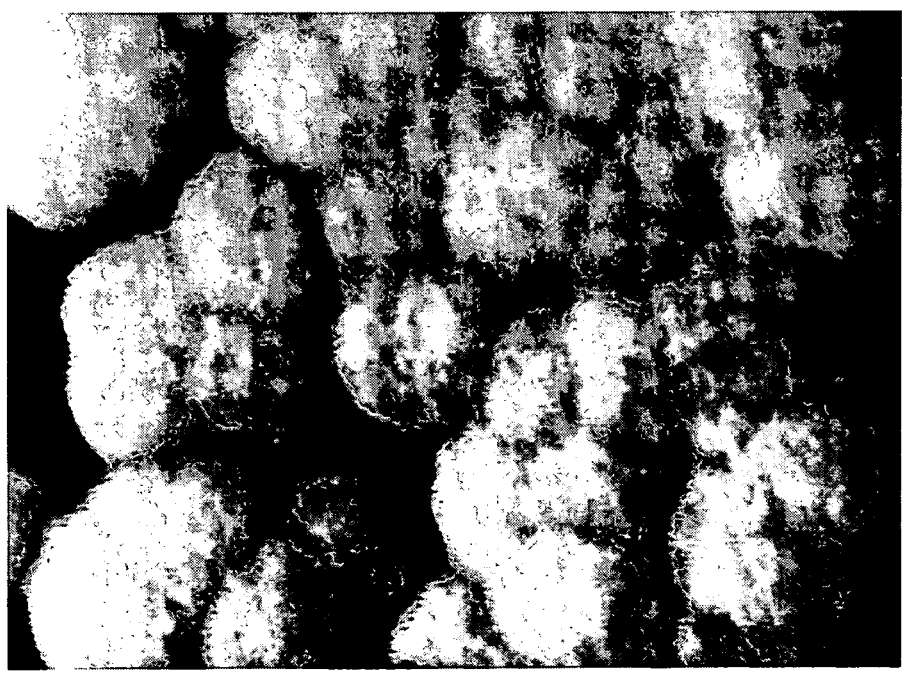
FIG. 3 is a scanning electron micrograph showing the external structure of the calcium phosphates structure according to Example 1 of the present invention.

The PESF having undergone the step in section (D) above was immersed in 30 ml of 1.5SBF (pH 7.4) contained in a polystyrene bin at 36.5° C. for 24 hours, while being hung with a clip. That is, 1.5SBF was used as a calcium phosphates growing solution. Hydroxyapatites were formed on the PESF. It is considered that calcium phosphates fine particles were deposited on the surface of the PESF in the step in section (D) above, and hydroxyapatites grew around the calcium phosphates fine particles as seeds in the 1.5SBF of the section (E). Scanning electron micrographs of the surface of the base material are shown in FIGS. 2 and 3.

Comparative Example 1

Steps in Comparative Example 1 were carried out as in Example 1, but the steps (B) through (D) were not carried out. Specifically, 1.5SBF was prepared by the step in section (A) above. Then, without the step in section (D), PESF was directly immersed at 36.5° C. for 24 hours, while being hung with a clip, in 30 ml of 1.5SBF contained in a polystyrene bin. No hydroxyapatites grew on the PESF (not shown).

It is considered that this occurred because calcium phosphates fine particles were not made deposited on the PESF.

Example 2

Through the steps which are the same as the steps (A) through (C) in Example 1, calcium phosphates fine particles were stabilized.

In the placement step of section (D) above, one piece of salmon roe (approximately 5 mm in diameter) was immersed as a base material, instead of the PESF, and allowed to stand at 36.5° C. for 30 minutes (Deposition of calcium phosphates fine particles on the salmon roe: placement step).

Next, the salmon roe was put in a polystyrene bin containing 30 ml of 1.5SBF therein, and immersed at 36.5° C. for 14 days (growing step). 1.5SBF was replaced by another fresh one once every two days.

Figure 4:
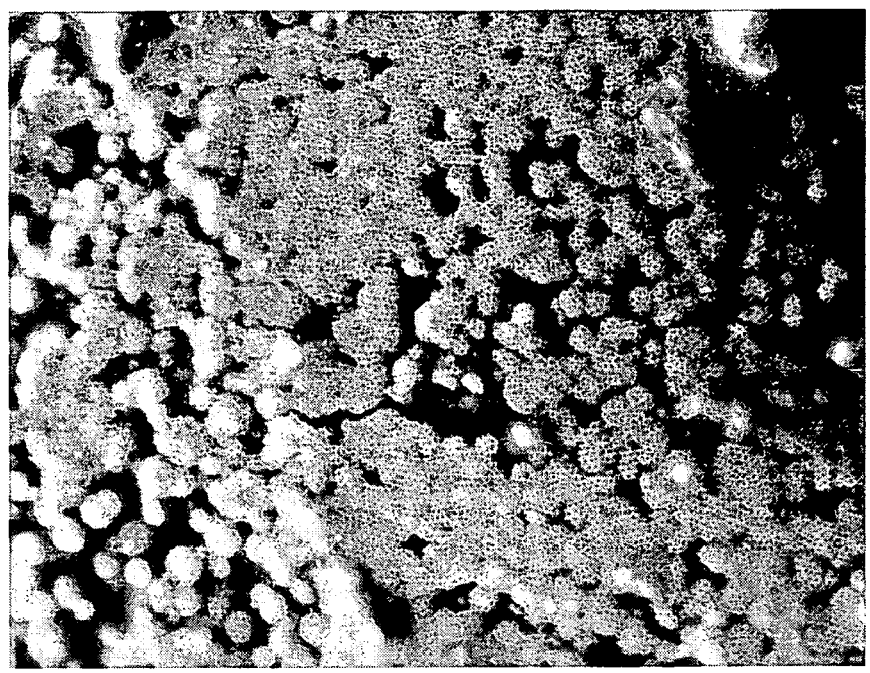
FIG. 4 is a scanning electron micrograph showing the external structure of a calcium phosphates structure according to Example 2 of the present invention.
Figure 5:
FIG. 5 is a scanning electron micrograph showing the external structure of the calcium phosphates structure according to Example 2 of the present invention.

Thereafter, the salmon roe was taken out of it and the surface of the salmon roe was observed through a scanning electron microscope. As a result, it was confirmed that hydroxyapatites were formed in such a manner that the surface of the salmon roe was coated with hydroxyapatites. Scanning electron micrographs are shown in FIGS. 4 and 5.

Example 3

Figure 6:
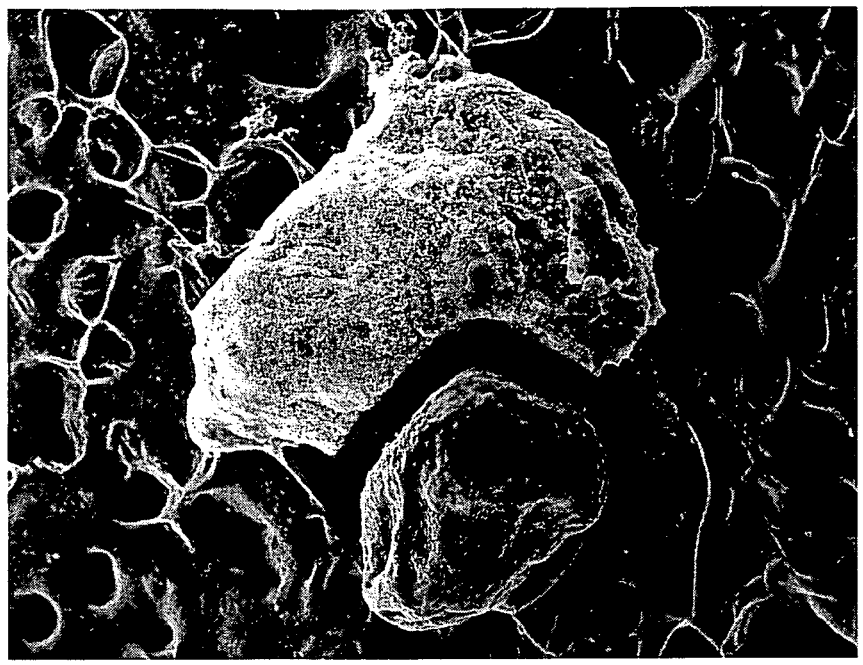
FIG. 6 is a scanning electron micrograph showing the external structure of a calcium phosphates structure according to Example 3 of the present invention.
Figure 7:
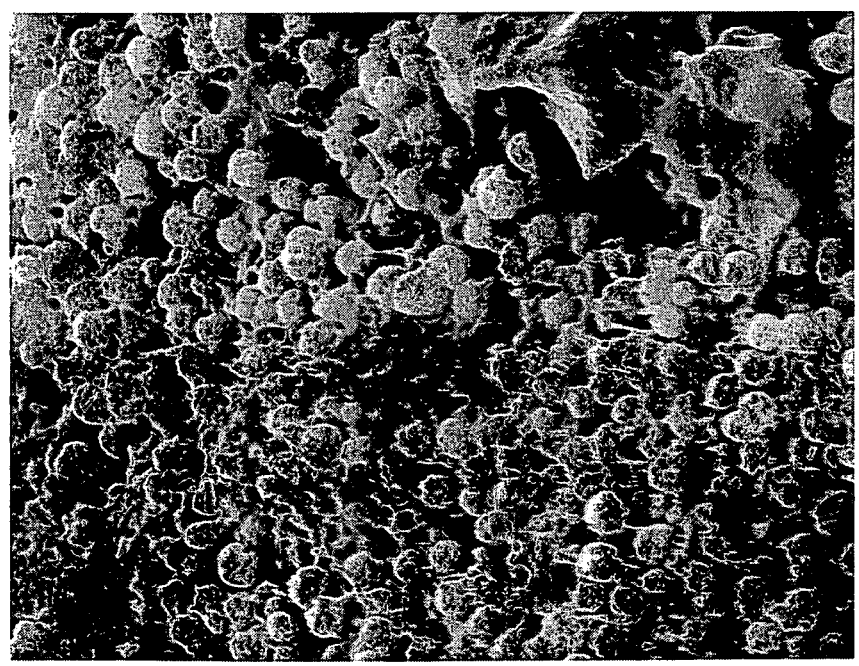
FIG. 7 is a scanning electron micrograph showing the external structure of the calcium phosphates structure according to Example 3 of the present invention.

Steps in Example 3 were carried out as in Example 2, but some pieces of cod roe (approximately 0.5 mm in diameter) were used instead of the salmon roe. As a result, it was confirmed that hydroxyapatites were formed in such a manner that the surface of the cod roe was coated with hydroxyapatites. Scanning electron micrographs are shown in FIGS. 6 and 7.

Example 4

Operations in Example 4 were performed as in Example 1, but 1.5SBF was replaced by 1.0SBF as a calcium-phosphates-growing solution in the step of section (E) above and a time for immersion into the calcium-phosphates-growing solution was changed.

Specifically, the PESF was immersed at 36.5° C. for 4 days in 30 ml of 1.0SBF, which is described in section (F) below, contained in a polystyrene bin, while being hung with a clip. 1.0SBF was replaced by another fresh one once every two days. Hydroxyapatites were formed on the base material (data are not shown).

(F) Preparation of 1.0SBF

In 700 mL of distilled water were dissolved 7.996 g of NaCl, 0.350 g of NaHCO3, 0.224 g of KCl, 0.228 g of K2HPO4.3H2O, 0.305 g of MgCl2.6H2O, 35 ml of 1M hydrochloric acid, 0.278 g of CaCl2, 0.071 g of Na2SO4, 6.057 g of tris(hydroxymethyl)aminomethane. The resulting solution was adjusted with 1M hydrochloric acid to be pH 7.4 at 36.5° C., in order to prepare 1.0SBF whose total volume became 1 L.

Example 5

The following operations were performed at room temperature (25° C.).

The solution in section (B) above was filtered stepwise through filter papers having a pore diameter of 10 μm, 1 μm, and 0.2 μm, respectively (OMNIPORE™, hydrophilic PTFE-type membrane filter manufactured by MILLIPORE) (stabilizing step). Thereafter, the filter papers were sufficiently dried in an incubator at 36.5° C.

After the filtration, the filter papers having a pore diameter of 1 μm, and 0.2 μm were each immersed in 50 ml of distilled water, while an ultrasonic washing machine was used for 5 minutes so that calcium phosphates fine particles remaining on the surfaces of the filter papers by filtration were dispersed into the distilled water. The resulting dispersed solutions are dispersed solutions G and H, respectively.

30 ml of the dispersed solution G and 30 ml of the dispersed solution H were filled in polystyrene bins, respectively. PESFs were immersed in the dispersed solutions at 36.5° C. for 24 hours, while being hung with clips (placement step). The PESFs immersed in the dispersed solutions G and H are a base material G and a base material H, respectively.

The base materials G and H that had undergone the above step were each immersed at 36.5° C. for 24 hours in 30 ml of 1.5SBF contained in a polystyrene bin, while being hung with a clip. Hydroxyapatites were formed on the surfaces of the base materials G and H (data are not shown). It is considered that in the above step, calcium phosphates fine particles were deposited on the surface of the base material, and hydroxyapatites were grown in 1.5SBF around the calcium phosphates fine particles as seeds.

Example 6

Operations were performed as in Example 1, but 1.5SBF was replaced by 1.0SBF in section (F) above as a fine-particle-forming solution in section (B) above.

As a result, hydroxyapatites were formed on the surfaces of PESFs (data are not shown).

Comparative Example 2

Operations were performed as in Example 1, but the solution obtained by the operation in section (B) above was used as a dispersed solution right after the pH adjustment, without the stabilizing step (step in section (C) above). Hydroxyapatites were formed on the surfaces of PESFs (data are no shown).

In the present comparative example, similar operations were performed, but 1.5SBF was replaced by 1.0SBF in section (F) above as a calcium-phosphates-growing solution. As a result, hydroxyapatites were formed on the surfaces of PESFs (data are not shown).

Comparative Example 3

The solution obtained by the operation in section (B) above was left for 24 hours without undergoing the stabilizing step (step in section (C) above). A white precipitate was found. By using the obtained solution, operations in sections (D) and (E) above were performed as in Example 1. As a result, hydroxyapatites were not formed on the surfaces of the PESFs (data are not shown).

The white precipitate is considered to be a precipitate generated as a result of the growth of the calcium phosphates fine particles. That is, it is considered that without the stabilizing step, calcium phosphates fine particles grew, aggregate, and precipitate, and, as a result, the calcium phosphates fine particles lost solid phase forming activity.

In the present comparative example, similar operations were performed, but 1.5SBF was replaced by 1.0SBF in section (F) above as a calcium-phosphates-growing solution. As a result, hydroxyapatites were not formed (data are not shown).

Example 7

Operations (placement step and growing step) were performed as in Example 4, but the solution in section (B) above was replaced by 1.0SBF described in section (I) below as a fine-particle-forming solution, and the fine-particle-forming solution was stabilized by a stabilizing step described in section (K) below, not by the stabilizing step in section (C) above.

As a result, hydroxyapatites were formed on the PESF (data are not shown).

(I) pH Adjustment

Tris(hydroxymethyl)aminomethane was added to 1.0SBF in section (F) above so that pH of the resulting solution was increased up to 8.5. The solution became whitely turbid. Then, by using hydrochloric acid, the pH of the solution was decreased to 7.8. Approximately pH 7.8 is a point at which the solution becomes limpid without white turbidity.

(K) Stabilizing Step

The following operations were performed at room temperature (25° C.).

The solution in section (I) above was overfilled in a dialysis tube (RC dialysis tube: pore 6, regenerated cellulose film, manufactured by Spectrum) having a molecular weight cut off of 1000, and one end of the dialysis tube was secured with a weighted closer, and the other end was secured with a closer with no weight. The dialysis tube was allowed to stand upright in a reservoir containing 2000 ml of distilled water. The distilled water in the reservoir was slowly stirred with a stirrer. The distilled water in the reservoir was replaced by fresh distilled water 1 hour later and 3 hours later. After a lapse of further 4 hours, the dialysis was completed.

Example 8

Operations were performed as in Example 7, but the solution in section (I) above was replaced by 0.5SBF described in section (J) below as a fine-particle-forming solution. As a result, hydroxyapatites were formed on the PESF (data are not shown).

(J) Preparation of 0.5SBF and pH Adjustment

In 700 mL of distilled water were dissolved 3.998 g of NaCl, 0.175 g of NaHCO3, 0.112 g of KCl, 0.114 g of K2HPO4.3H2O, 0.153 g of MgCl2.6H2O, 17.5 ml of 1M hydrochloric acid, 0.139 g of CaCl2, 0.036 g of Na2SO4, 3.028 g of Tris(hydroxymethyl)aminomethane. The resulting solution was adjusted with 1M hydrochloric acid to be pH 7.4 at 36.5° C., in order to prepare 0.5SBF whose total volume became 1 L.

Tris(hydroxymethyl)aminomethane was added to the above 0.5SBF so that pH of the resulting solution was increased up to 9.6. The solution became whitely turbid.

Then, by using hydrochloric acid, the pH of the solution was decreased to 8.8. Approximately pH 8.8 is a point at which the solution becomes limpid without white turbidity.

Example 9

Through the following operations, a pattern of hydroxyapatites was formed.

After the surface of a silicone base material (10 mm×15 mm×1 mm) was treated with hexamethyldisilazane, a positive novolac resist was screen-printed thereon into a rectangular pattern and heated at 90° C. for 30 minutes. Then, an area having the rectangular pattern formed thereon was irradiated with light of a high pressure mercury lamp at 25 W/cm2 for 1.5 seconds via a photomask so that a pattern of parallel lines, which will be described later, was formed. The sample irradiated with light was immersed at 25° C. for 60 seconds in a developer made from an aqueous solution of tetramethylammonium hydroxide so that portions to be dissolved in the developer were dissolved. The sample was washed with pure water and then heated at 120° C. for 30 minutes. In this manner, obtained was the silicone base material having a pattern of parallel lines part of which is exposed and has a line width of 1 μm and line-to-line spacing of 1 μm, and the other part of which is coated with the resin.

The thus obtained base material was immersed at 36.5° C. for 24 hours in the dispersed solution obtained in the step of section (C) above (placement step).

The base material on which the calcium phosphates fine particles were deposited was immersed in acetone, so that the resist was dissolved.

Thereafter, the base material was immersed in the 1.5SBF of section (A) above used as a calcium-phosphates-growing solution, so that hydroxyapatites were grown.

On the surface of the base material, a pattern of hydroxyapatites was formed, and the pattern of hydroxyapatites, which were formed in a no-resist area, correctly reproduced the resist pattern.

Example 10

A long-term preservation of a calcium phosphates fine particles-dispersed solution was examined.

1000 ml of 1.0SBF was adjusted to be pH 8.5 at 25° C. by addition of tris(hydroxymethyl)aminomethane thereto. Right after the adjustment, the resulting solution was filtered through a filter paper (ISOPORE™) (polycarbonate track-etched membrane filter manufactured by MILLIPORE) having a pore diameter of 0.05 μm. After the filtration, NaCl was removed by passing distilled water through the filter paper, and moisture was then removed by passing ethanol through the filter paper. Thereafter, the filter paper was immersed in 200 ml of ethanol contained in a polystyrene screw cap bottle, and calcium phosphates fine particles on the surface of the filter paper were sufficiently dispersed in ethanol by using an ultrasonic washing machine for 30 minutes.

The thus obtained calcium phosphates fine particles-dispersed ethanol solution was divided in four screw cap bottles, 50 ml each. The first, second, third, and fourth bottles were subjected to the operation below, immediately thereafter, one week later, two weeks later, and four weeks later, respectively.

Ethanol was removed from the calcium phosphates fine particles-dispersed ethanol solution by using an evaporator, and substituted by distilled water. To 50 ml of the thus obtained calcium phosphates fine particles-dispersed aqueous solution was added 20 μl of polylactic acid (PLA) fine particles-dispersed aqueous solution (purchased from COREFRONT corporation; product number: 11-00-203) having a particle diameter of 2 μm, so that seeding was carried out around the surfaces of the PLA fine particles (placement step). A period for the seeding was one day.

The PLA fine particles subjected to seeding were collected by filtering through a filter paper (OMNIPORE™, hydrophilic PTFE membrane filter manufactured by MILLIPORE) having a pore diameter of 0.1 μm. While the filter paper was immersed in 1.0SBF (pH 7.4 at 36.5° C.), dispersion was sufficiently carried out by 30-minutes ultrasonication. A period for immersion was one week (growing step). On the third day of the immersion period, i.e. a halfway point thereof, 1.0SBF was replaced. A replacement process was performed as in the process performed after the seeding. That is, the PLA fine particles were collected by filtering through the hydrophilic PTFE-type filter paper having a pore diameter of 0.1 μm. Then, while the filter paper was immersed in 30 ml of 1.0SBF, dispersion was sufficiently carried out by 30-minutes ultrasonication.

After the end of the 1.0SBF immersion period, the PLA fine particles were collected by filtering through the hydrophilic PTFE-type filter paper having a pore diameter of 0.1 μm. Then, NaCl was removed by passing distilled water through the filter paper, and the PLA fine particles were dried in an incubator at 36.5° C. Thereafter, the surfaces of the PLA fine particles were observed through SEM (scanning electron microscope).

It was found that a thin film of hydroxyapatites was formed on the surface of the PLA fine particle that is a base material, regardless of an elapsed time after the preparation of the calcium phosphates fine particles-dispersed ethanol solution. From this result, it was verified that the method for stabilizing calcium phosphates fine particles according to the present invention allows calcium phosphates fine particles to be stably preserved for long periods while retaining a high solid phase forming activity.

Example 11

Six different types of solutions, which were prepared from the reduction of weights of reagents contained in 1.0SBFs by half as shown in Table 1, were used as the fine-particle-forming solutions. The pH of the solutions was adjusted as shown in Table 1.

TABLE 1

|  | Adjusted pH |
|---|---|
| (1) NaCl reduced by half (3.998 g) | 8.50 |
| (2) $MgCl_2 6H_2O$ reduced by half (0.153 g) | 8.50 |
| (3) KCl reduced by half (0.112 g) | 8.50 |
| (4) $CaCl_2$ reduced by half (0.139 g) | 9.10 |
| (5) $K_2HPO_4 3H_2O$ reduced by half (0.114 g) | 8.90 |
| (6) $CaCl_2$ and $K_2HPO_4 3H_2O$ each reduced by half | 9.50 |

The fine-particle-forming solutions, each 1000 ml, were filtered though filter papers (ISOPORE™, polycarbonate track-etched membrane filter manufactured by MILLIPORE) having a pore diameter of 0.05 μm (stabilizing step). Thereafter, each of the filter papers was immersed in 200 ml of ethanol so that calcium phosphates fine particles on the filter papers were dispersed therein.

Ethanol that is a solvent of the resulting dispersed solution was substituted by distilled water by using an evaporator. To the dispersed solution was added 20 μl of polylactic acid (PLA) fine particles (2 μm in particle diameter), and the PLA fine particles were immersed for one day (placement step).

The PLA fine particles around which calcium phosphates fine particles were deposited as seeds were collected by filtering through a hydrophilic PTFE-type filter paper having a pore diameter of 0.1 μm. The collected PLA fine particles were dispersed in 1.0SBF (pH 7.4), and immersed therein at 36.5° C. for one week (growing step). Thereafter, the PLA fine particles were collected by filtering through a hydrophilic PTFE-type filter paper having a pore diameter of 0.1 μm, and the surfaces of the PLA fine particles were observed and analyzed through SEM (scanning electron microscope)/EDX (energy dispersive X-ray spectrometer).

Figure 8A:
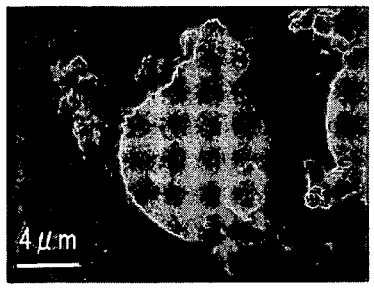
FIG. 8(a) is a scanning electron micrograph showing the external structure of a calcium phosphates structure according to (1) of Example 11 of the present invention.
Figure 8B:
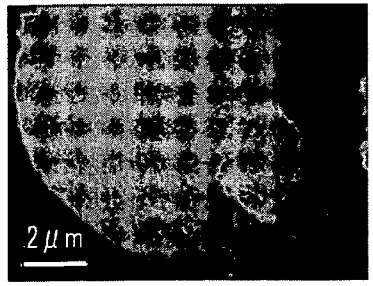
FIG. 8(b) is a scanning electron micrograph showing the external structure of the calcium phosphates structure according to (1) of Example 11 of the present invention.
Figure 8C:
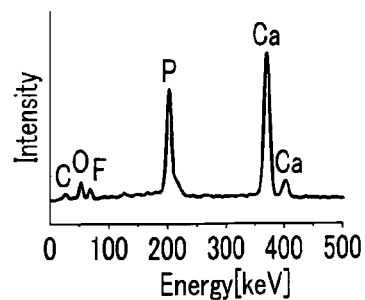
FIG. 8(c) is a chart showing EDX analysis result of the external structure of the calcium phosphates structure according to (1) of Example 11 of the present invention.

(1) FIGS. 8(a), 8(b), and 8(c) show the result obtained by using the fine-particle-forming solution in which a NaCl concentration was reduced by half.

Figure 9A:
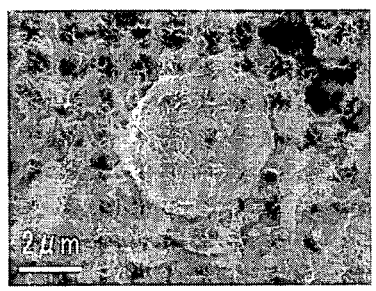
FIG. 9(a) is a scanning electron micrograph showing the external structure of a calcium phosphates structure according to (2) of Example 11 of the present invention.
Figure 9B:
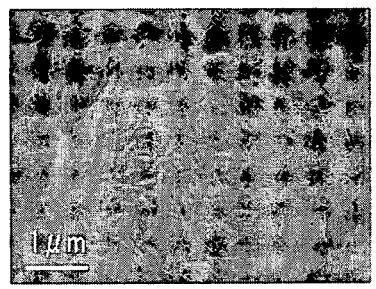
FIG. 9(b) is a scanning electron micrograph showing the external structure of the calcium phosphates structure according to (2) of Example 11 of the present invention.
Figure 9C:
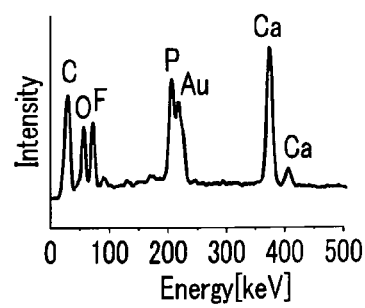
FIG. 9(c) is a chart showing EDX analysis result of the external structure of the calcium phosphates structure according to (2) of Example 11 of the present invention.

(2) FIGS. 9(a), 9(b), and 9(c) show the result obtained by using the fine-particle-forming solution in which a MgCl2 concentration was reduced by half.

Figure 10A:
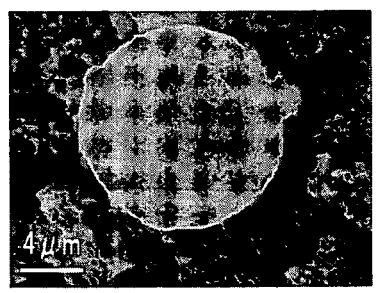
FIG. 10(a) is a scanning electron micrograph showing the external structure of a calcium phosphates structure according to (3) of Example 11 of the present invention.
Figure 10B:
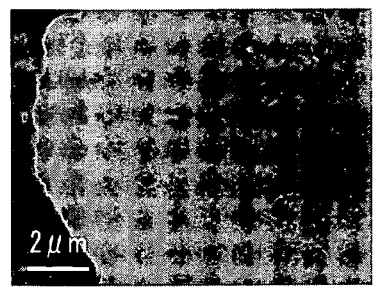
FIG. 10(b) is a scanning electron micrograph showing the external structure of the calcium phosphates structure according to (3) of Example 11 of the present invention.
Figure 10C:
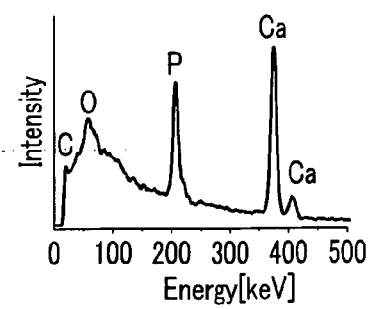
FIG. 10(c) is a chart showing EDX analysis result of the external structure of the calcium phosphates structure according to (3) of Example 11 of the present invention.

(3) FIGS. 10(a), 10(b), and 10(c) show the result obtained by using the fine-particle-forming solution in which a KCl concentration was reduced by half.

Figure 11A:
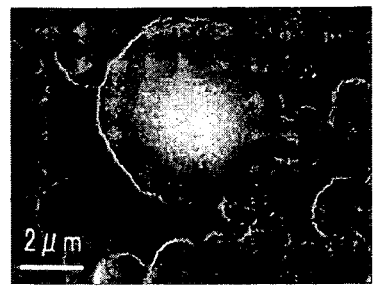
FIG. 11(a) is a scanning electron micrograph showing the external structure of a calcium phosphates structure according to (4) of Example 11 of the present invention.
Figure 11B:
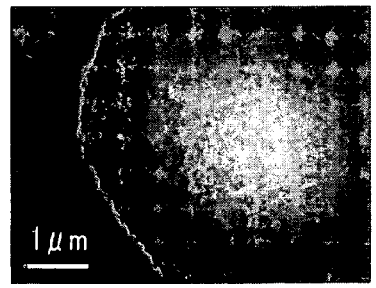
FIG. 11(b) is a scanning electron micrograph showing the external structure of the calcium phosphates structure according to (4) of Example 11 of the present invention.
Figure 11C:
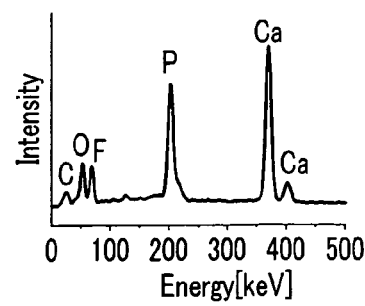
FIG. 11(c) is a chart showing EDX analysis result of the external structure of the calcium phosphates structure according to (4) of Example 11 of the present invention.

(4) FIGS. 11(a), 11(b), and 11(c) show the result obtained by using the fine-particle-forming solution in which a CaCl2 concentration was reduced by half.

Figure 12A:
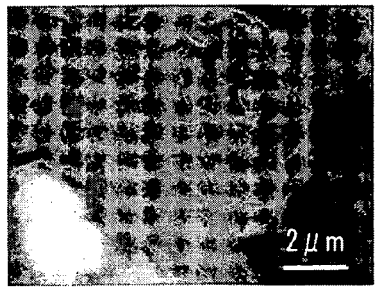
FIG. 12(a) is a scanning electron micrograph showing the external structure of a calcium phosphates structure according to (5) of Example 11 of the present invention.
Figure 12B:
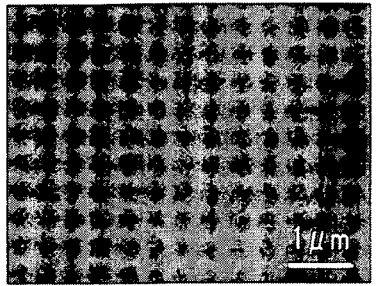
FIG. 12(b) is a scanning electron micrograph showing the external structure of the calcium phosphates structure according to (5) of Example 11 of the present invention.
Figure 12C:
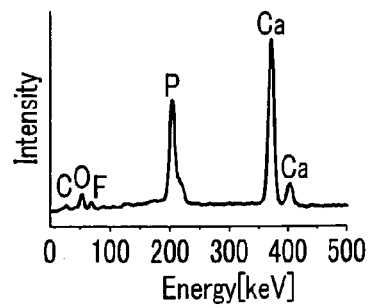
FIG. 12(c) is a chart showing EDX analysis result of the external structure of the calcium phosphates structure according to (5) of Example 11 of the present invention.

(5) FIGS. 12(a), 12(b), and 12(c) show the result obtained by using the fine-particle-forming solution in which a K2HPO4 concentration was reduced by half.

Figure 13A:
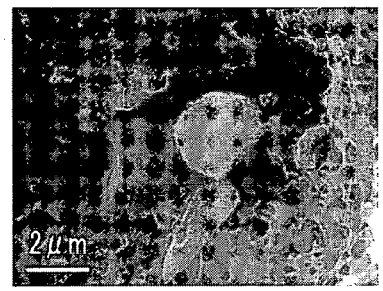
FIG. 13(a) is a scanning electron micrograph showing the external structure of a calcium phosphates structure according to (6) of Example 11 of the present invention.
Figure 13B:
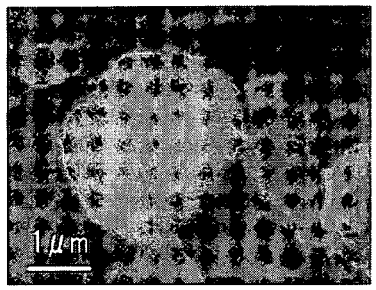
FIG. 13(b) is a scanning electron micrograph showing the external structure of the calcium phosphates structure according to (6) of Example 11 of the present invention.
Figure 13C:
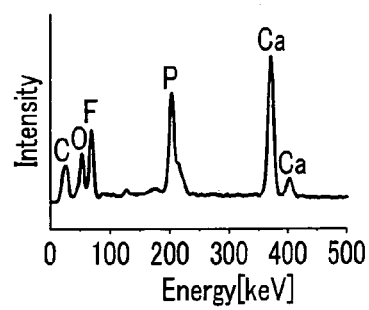
FIG. 13(c) is a chart showing EDX analysis result of the external structure of the calcium phosphates structure according to (6) of Example 11 of the present invention.

(6) FIGS. 13(a), 13(b), and 13(c) show the result obtained by using the fine-particle-forming solution in which a CaCl2 and K2HPO4 concentrations were reduced by half.

From the results of (1) through (6), it was found that even when the solution in which the concentration of part of constituents in the composition of the 1.0SBF was reduced by half was used as the fine-particle-forming solution, hydroxyapatites were formed around the surface of the PLA fine particle as the base material in such a manner that calcium phosphates fine particles formed in the fine-particle-forming solution become seeds.

Comparative Example 4

1.0SBFs (each 200 ml) respectively adjusted to be pH 8.00 and 8.30 were allowed to stand for 16 days.
The 1.0SBFs having the above pH values were each filtered through hydrophilic PTFE-type filter papers having a pore diameter of 10 μm. Thereafter, each of the filter papers was immersed in 200 ml of ethanol so that calcium phosphates fine particles deposited on the filter paper were dispersed therein. 50 ml of the calcium phosphates fine particles-dispersed ethanol solution was substituted by 50 ml of distilled water to be a calcium phosphates fine particles-dispersed distilled water solution by using an evaporator.

To the calcium phosphates fine particles-dispersed distilled water solution was added 20 μl of PLA fine particles having a particle diameter of 2 μm, and the PLA fine particles were immersed for one day. The PLA fine particles were collected by filtering through a hydrophilic PTFE-type filter paper having a pore diameter of 0.1 μm. The collected PLA fine particles were dispersed in 1.0SBF (pH 7.4), and immersed therein at 36.5° C. for one week. Thereafter, the PLA fine particles were collected by filtering through a hydrophilic PTFE-type filter paper having a pore diameter of 0.1 μm, the surfaces of the PLA fine particles were observed and analyzed through SEM/EDX.

Figure 14:
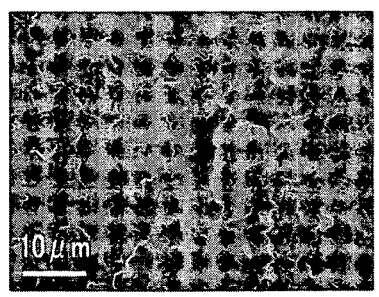
FIG. 14 is a scanning electron micrograph of calcium phosphates fine particles obtained by allowing 1.0SBF adjusted to be pH 8.00 to stand for 16 days in Comparative Example 4.

FIG. 14 shows an SEM image of the calcium phosphates fine particles obtained by allowing the 1.0SBF adjusted to be pH 8.00 to stand for 16 days. A particle diameter of the fine particles was approximately in the range from 2 μm to 6 μm.

Figure 15:
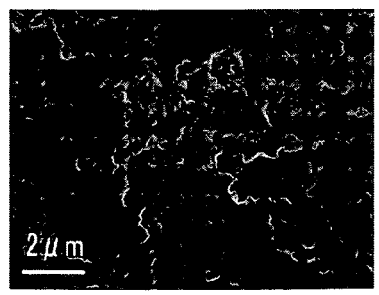
FIG. 15 is a scanning electron micrograph of calcium phosphates fine particles obtained by allowing 1.0SBF adjusted to be pH 8.30 to stand for 16 days in Comparative Example 4.

FIG. 15 shows an SEM image of the calcium phosphates fine particles obtained by allowing the 1.0SBF adjusted to be pH 8.30 to stand for 16 days. A particle diameter of the fine particles was approximately in the range from 200 nm to 400 nm.

Figure 16A:
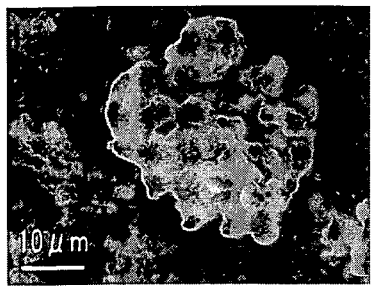
FIG. 16(a) is a scanning electron micrograph showing the result of using as seeds the calcium phosphates fine particles obtained by allowing 1.0SBF adjusted to be pH 8.00 to stand for 16 days in Comparative Example 4.
Figure 16B:
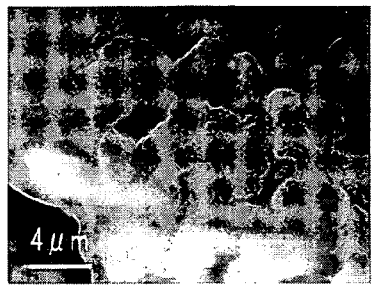
FIG. 16(b) is a scanning electron micrograph showing the result of using as seeds the calcium phosphates fine particles obtained by allowing 1.0SBF adjusted to be pH 8.00 to stand for 16 days in Comparative Example 4.
Figure 16C:
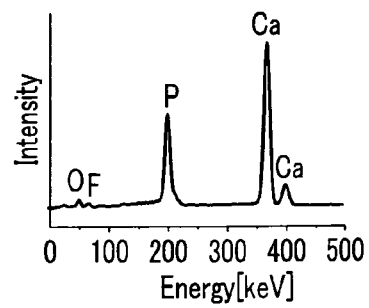
FIG. 16(c) is a chart showing EDX analysis result in the case of using as seeds the calcium phosphates fine particles obtained by allowing 1.0SBF adjusted to be pH 8.00 to stand for 16 days in Comparative Example 4.

FIGS. 16(a), 16(b), and 16(c) show the result of the attempt to grow hydroxyapatites around the surfaces of the PLA fine particles in such a manner that the calcium phosphates fine particles obtained by allowing the 1.0SBF adjusted to be pH 8.00 to stand for 16 days become seeds. From FIGS. 16(a) and 16(b), it is found that some PLAs coaggulated with the growth of hydroxyapatites.

Figure 17A:
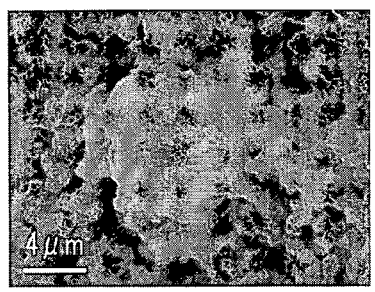
FIG. 17(a) is a scanning electron micrograph showing the result of using as seeds the calcium phosphates fine particles obtained by allowing 1.0SBF adjusted to be pH 8.30 to stand for 16 days in Comparative Example 4.
Figure 17B:
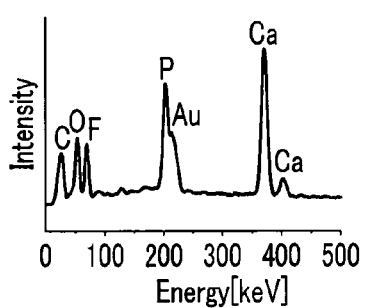
FIG. 17(b) is a chart showing EDX analysis result in the case of using as seeds the calcium phosphates fine particles obtained by allowing 1.0SBF adjusted to be pH 8.30 to stand for 16 days in Comparative Example 4.

FIGS. 17(a) and 17(b) show the results of the attempt to grow hydroxyapatites around the surfaces of the PLA fine particles in such a manner that the calcium phosphates fine particles obtained by allowing the 1.0SBF adjusted to be pH 8.30 to stand for 16 days become seeds. From FIG. 17(a), although it is found that hydroxyapatites were grown around the surfaces of the PLAs, rough agglomerations existed.

As is apparent from the above results, the calcium phosphates fine particles obtained from 1.0SBFs (fine-particle-forming solutions) after a long time has elapsed since pH adjustment grow into large particles, and therefore are not suitable as fine particles that serve as seeds for the growth of hydroxyapatites around a base material which is not sufficiently larger than the grown calcium phosphates fine particles.

Example 12

To 1000 ml of 1.0SBF was added tris(hydroxymethyl)aminomethane at 25° C. so that the 1.0SBF is adjusted to be pH 8.50 (fine-particle-forming solution). The resulting solution was filtered through a polycarbonate filter paper having a pore diameter of 0.05 μm (stabilizing step), and the filter paper was immersed in 200 ml of ethanol so that calcium phosphates fine particles deposited on the filter paper were dispersed therein.

5 ml of ethanol of the calcium phosphates fine particles-dispersed ethanol solution was removed by using an evaporator and substituted by 50 ml of distilled water. To the obtained calcium phosphates fine particles-dispersed distilled water solution was added 20 μl of PLA fine particles having a particle diameter of 2 μm, and the PLA fine particles were immersed for one day (placement step). The PLA fine particles were collected by filtering through a hydrophilic PTFE-type filter paper having a pore diameter of 0.1 μm, dispersed in three types of 1.0SBFs adjusted to be pH 7.40, 7.50, and 7.60, respectively, and immersed therein at 36.5° C. for 4 days (growing step). On the second day, the 1.0SBFs adjusted to have the above pH values, respectively, were replaced. The PLA fine particles were collected by filtering through a hydrophilic PTFE-type filter paper having a pore diameter of 0.1 μm, and the surfaces of the PLA fine particles were observed through SEM.

Figure 18:
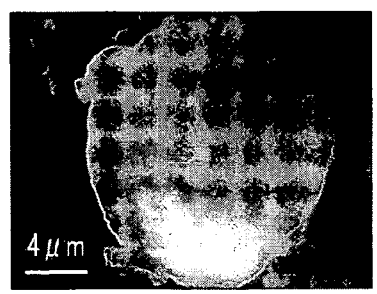
FIG. 18 is a scanning electron micrograph showing the result of using 1.0SBF adjusted to be pH 7.40 as a growing solution in Example 12 of the present invention.
Figure 19:
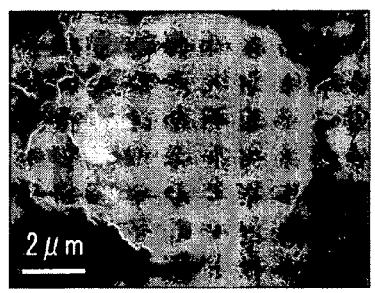
FIG. 19 is a scanning electron micrograph showing the result of using 1.0SBF adjusted to be pH 7.50 as a growing solution in Example 12 of the present invention.
Figure 20:
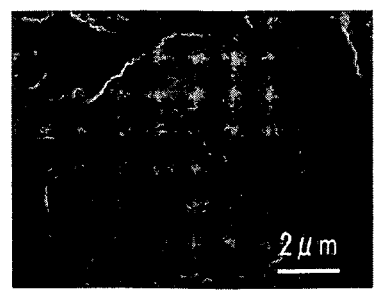
FIG. 20 is a scanning electron micrograph showing the result of using 1.0SBF adjusted to be pH 7.60 as a growing solution in Example 12 of the present invention.

FIGS. 18, 19, and 20 show the results obtained by using the 1.0SBFs respectively adjusted to be pH 7.40, pH 7.50, and pH 7.60, as the growing solutions. It was found that hydroxyapatites excellently grew around the surface of PLA with the use of all of the 1.0SBFs having the above pH values as the growing solutions.

Comparative Example 5

After 1.5SBFs were adjusted to be pH 7.00, 7.20, 7.40, 7.60, 7.80, and 8.00 at 36.5° C., respectively, the generation of calcium phosphates fine particles was identified in the time-course examination based on Tyndall phenomenon.

The results are shown in FIG. 21. As is apparent from FIG. 21, Tyndall phenomenon was clearly observed in the 1.5SBF having pH 8.00 right after the pH adjustment, and white turbidity and a white precipitate were observed 3 hours after the pH adjustment. In the case of the 1.5SBF having pH 7.80, Tyndall phenomenon was clearly observed 1 hour after the pH adjustment, and a white precipitate was observed 6 hours after the pH adjustment. The amount of white precipitate increased over time. In the case of 1.5SBF having pH 7.60, Tyndall phenomenon was vaguely observed 53 hours after the pH adjustment, and a white precipitate was observed 77 hours after the pH adjustment. At the observations 149 hours and 508 hours after the pH adjustment, it was found that the amount of white precipitate further increased over time. In the case of 1.5SBF having pH 7.40, a white precipitate generated after the SBF was allowed to stand for 508 hours, and Tyndall phenomenon was observed. On the other hand, in the cases of 1.5SBF having pH 7.00 and the 1.5SBF having pH 7.20, Tyndall phenomenon was not observed 508 hours after the pH adjustment.

From the above results, it was confirmed that the SBFs were unsuitable for the preservation of calcium phosphates fine particles since seeds grow when calcium phosphates fine particles generated, and the calcium phosphates fine particles further grow until a white precipitate generated.

Further, the SBFs, which are susceptible to bacteria, become turbid even when no calcium phosphates fine particles are precipitated in the SBFs. Still further, the SBFs contain various salts, including NaCl, in high concentrations, which is a cause of metal corrosion. Therefore, metal cannot be used for a container of the SBFs. On the contrary, the calcium phosphates fine particles of the present invention can be preserved in the form of powder and easily dispersed in a solution. Further, since the calcium phosphates fine particles are insoluble in water, a calcium phosphates fine particles dispersed solution is not corrosive to metal. Furthermore, calcium phosphates fine particles can be easily dispersed in a liquid other than water, such as alcohol and acetone. If the SBFs are preserved as they are, a salt is precipitated in the SBFs because of moisture evaporation. This means that the SBFs must be preserved in enclosed state, which makes it difficult to handle the SBFs. In a case where the calcium phosphates fine particles-dispersed solution is used, the occurrence of evaporation of the solution is solved merely by adding water.

Example 13

1000 ml of 1.0SBF adjusted to be pH 7.4 at 36.5° C. was adjusted to be pH 8.5 by using tris(hydroxymethyl)aminomethane. Calcium phosphates fine particles (apatite seeds) generated in the above 1.0SBF. The 1.0SBF was filtered through a polycarbonate filter paper (manufactured by MILLIPORE) having a pore diameter of 0.05 μm right after the pH adjustment, so that the generated calcium phosphates fine particles were collected on the filter paper. After the filtration, ultrapure water and ethanol were filtered through the filter paper in this order, whereby NaCl and moisture were removed from the filter paper.

Thereafter, the filter paper was immersed in 200 ml of ethanol and subjected to an ultrasonic washing machine for 30 minutes, so that calcium phosphates fine particles (apatite seeds) deposited on the filter paper were dispersed in ethanol. In this state, the calcium phosphates fine particles (apatite seeds) were retained stably. After distilled water was added to the ethanol solution, the resulting solution was subjected to an evaporator to evaporate an ethanol content, so that calcium phosphates fine particles (apatite seeds) were dispersed in distilled water. Then, 0.2 mg of polylactic acid spherical particles (2 μm in diameter) were added to the resulting solution, and seeding was carried out. A period for the seeding was one day.

Figure 22A:
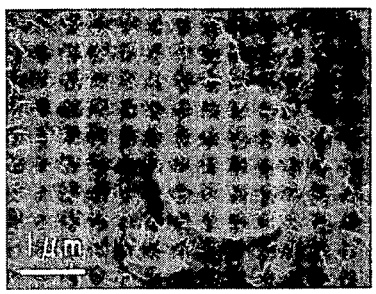
FIG. 22(a) is a scanning electron micrograph showing the result of the growth of hydroxyapatites by using a polylactic acid spherical particle as a base material in Example 13 of the present invention.
Figure 22B:
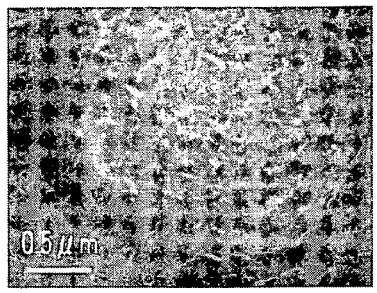
FIG. 22(b) is a scanning electron micrograph showing the result of the growth of hydroxyapatites by using a polylactic acid spherical particle as a base material in Example 13 of the present invention.
Figure 22C:
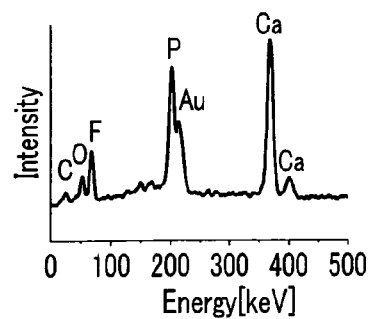
FIG. 22(c) is a chart showing EDX analysis result in a case where hydroxyapatites were grown by using a polylactic acid spherical particle as a base material in Example 13 of the present invention.

The polylactic acid spherical particles after the seeding were taken out by filtering through a hydrophilic PTFE-type filter paper having a pore diameter of 0.1 μm, and dispersed in 1.0SBF for the growth of hydroxyapatites. A period for the immersion in the 1.0SBF was one week. Thereafter, the polylactic acid spherical particles were taken out by filtration. Under SEM observation and EDX measurement, it was found that the surfaces of the polylactic acid spherical particles were uniformly covered with thin films of hydroxyapatites. FIGS. 22 (a) and 22(b) show SEM images, and FIG. 22(c) shows EDX analysis result.

The polylactic acid spherical particles on which surface hydroxyapatites were grown after the immersion in 1.0SBF were immersed in acetone to elute polylactic acid, thereby preparing a capsule of hydroxyapatites.

Figure 23A:
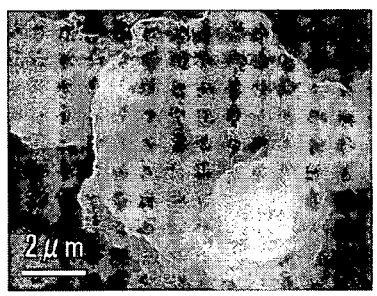
FIG. 23(a) is a scanning electron micrograph of a capsule of hydroxyapatites in Example 13 of the present invention.
Figure 23B:
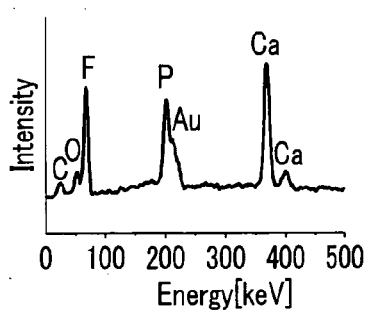
FIG. 23(b) is a chart showing EDX analysis result of the capsule of hydroxyapatites in Example 13 of the present invention.
Figure 24A:
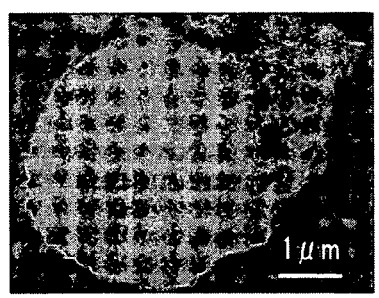
FIG. 24(a) is a scanning electron micrograph of a capsule of hydroxyapatites in Example 13 of the present invention.
Figure 24B:
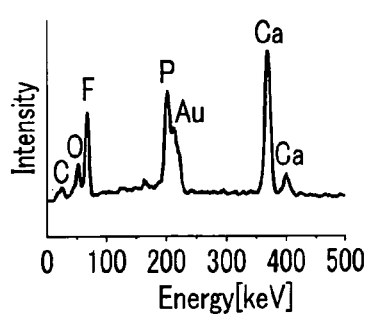
FIG. 24(b) is a chart showing EDX analysis result of the capsule of hydroxyapatites in Example 13 of the present invention.

FIGS. 23(a) and 23(b) show an SEM image and EDX analysis result of a hydroxyapatites thin film partially broken due to elution of polylactic acid, respectively. From FIG. 23(a), it is apparent that hydroxyapatites thin film has a hollow inside. FIGS. 24(a) and 24(b) show an SEM image and EDX analysis result of a capsule made from the hydroxyapatites thin film having a spherical shape maintained after elution of polylactic acid.

As described above, it is obvious that the present invention can be implemented in the form of a capsule made from a hydroxyapatites thin film and is very useful.

Example 14

Through multistep filtration, the stabilization of calcium phosphates fine particles was examined.

1000 ml of 1.0SBF was adjusted to be pH 8.5 by addition of tris(hydroxymethyl)aminomethane at 25° C. Right after the adjustment, the resulting solution was filtered through hydrophilic PTFE-type filer papers having a pore diameter of 10 μm, 1 μm, and 0.1 μm, and a polycarbonate filter paper having a pore diameter of 0.05 μm, in this order. After the filtration, NaCl was removed by passing distilled water through each of the filter papers, and moisture was then removed by passing ethanol through each of the filter papers. Thereafter, each of the filter papers was immersed in 200 ml of ethanol contained in a polystyrene screw cap bottle, and calcium phosphates fine particles on the surface of the filter papers were sufficiently dispersed in ethanol by using an ultrasonic washing machine for 30 minutes. By the above operations, four types of calcium phosphates fine particles-dispersed ethanol solutions were obtained.

To 150 ml of each of the calcium phosphates fine particles-dispersed ethanol solutions was added 50 ml of distilled water. Thereafter, an ethanol content of the resulting solution was evaporated through an evaporator, so that calcium phosphates fine particles (apatite seeds) were dispersed in 50 ml of distilled water. In this case, ethanol was substituted by water because polylactic acid (PLA) fine particles used as the base material are weak against an organic solvent. To 50 ml of each of the thus obtained calcium phosphates fine particles-dispersed aqueous solution was added 20 μl of polylactic acid (PLA) fine particles-dispersed aqueous solution (purchased from COREFRONT Corporation; product number: 11-00-203) having a particle diameter of 2 μm, so that seeding was carried out onto the surfaces of the PLA fine particles. A period for the seeding was one day.

The PLA fine particles subjected to seeding were collected by filtering through a hydrophilic PTFE-type filter paper having a pore diameter of 0.1 µm. While the filter paper was immersed in 1.0SBF (pH 7.4), dispersion was sufficiently carried out by 30-minutes ultrasonication. A period for immersion was one week (growing step). On the third day of the immersion period, i.e. a halfway point thereof, 1.0SBF was replaced. A replacement process was performed as in the process performed after the seeding. That is, the PLA fine particles were collected by filtering through the hydrophilic PTFE-type filter paper having a pore diameter of 0.1 µm. Then, while the filter paper was immersed in 30 ml of 1.0SBF, dispersion was sufficiently carried out by 30-minutes ultrasonication.

After the end of the 1.0SBF immersion period, PLA fine particles were collected by filtering through the hydrophilic PTFE-type filter paper having a pore diameter of 0.1 µm. Then, NaCl was removed by passing distilled water through the filter paper, and the PLA fine particles were dried in an incubator at 36.5° C. Thereafter, the surfaces of the PLA fine particles were observed and analyzed through SEM/EDX.

Figure 25A:
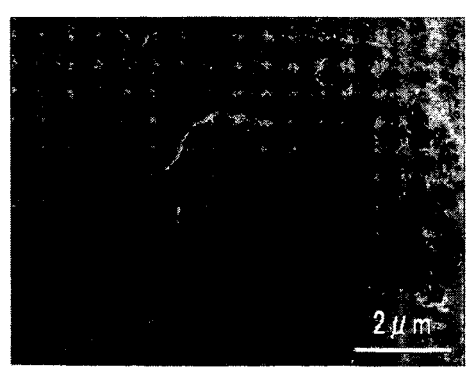
FIG. 25(a) is a scanning electron micrograph of the surface of a PLA fine particle in a case where seeds were calcium phosphates fine particles separated by a filter paper having a pore diameter of 0.1 μm in Example 14 of the present invention.
Figure 25B:
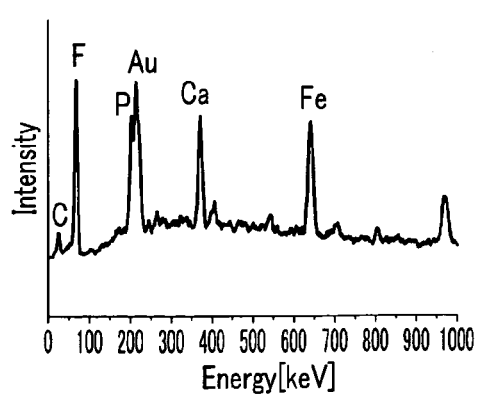
FIG. 25(b) is a chart of EDX analysis result of the surface of the PLA fine particle in a case where seeds were calcium phosphates fine particles separated by a filter paper having a pore diameter of 0.1 μm in Example 14 of the present invention.

FIGS. 25(a) and 25(b) show an SEM image and EDX analysis result of the surface of the PLA fine particle obtained in a case where seeds were a calcium phosphates fine particles separated by the filter paper having a pore diameter of 0.1 µm. From FIGS. 25(a) and 25(b), it was confirmed that hydroxyapatites grew on the surfaces of the PLA fine particle.

Figure 26:
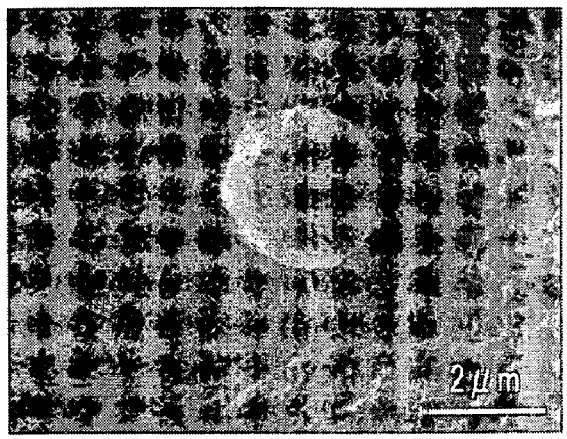
FIG. 26(a) is a scanning electron micrograph of the surface of a PLA fine particle in a case where seeds were calcium phosphates fine particles separated by a filter paper having a pore diameter of 0.05 μm in Example 14 of the present invention.
FIG. 26(b) is a chart of EDX analysis result of the surface of the PLA fine particle in a case where seeds were calcium phosphates fine particles separated by a filter paper having a pore diameter of 0.05 μm in Example 14 of the present invention.
Figure 26:
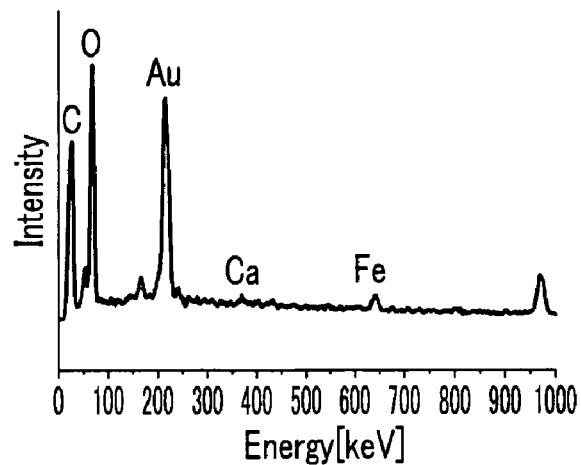

FIGS. 26(a) and 26(b) show an SEM image and EDX analysis result of the surface of the PLA fine particle obtained in a case where seeds were a calcium phosphates fine particles separated by the filter paper having a pore diameter of 0.05 µm. From FIGS. 26(a) and 26(b), it was found that the amount of hydroxyapatites grown around the surface of the PLA fine particle was much smaller than that of hydroxyapatites obtained by using the filter paper having a pore diameter of 0.1 µm.

Example 15

Most of the calcium phosphates fine particles formed in Example 14 was considered to be collected by the filter paper having a pore diameter of 0.1 µm. In order to verify this, a single-step filtration was examined.

1000 ml of 1.0SBF was adjusted to be pH 8.5 by addition of tris(hydroxymethyl)aminomethane at 25° C. At this moment, the 1.0SBF was limpid without white turbidity. Right after the pH adjustment, the 1.0SBF was filtered through a polycarbonate filter paper having a pore diameter of 0.05 µm. After the filtration, NaCl was removed by passing distilled water through the filter paper, and moisture was then removed by passing ethanol through the filter paper. Thereafter, the filter paper was immersed in 200 ml of ethanol contained in a polystyrene screw cap bottle, and calcium phosphates fine particles on the surface of the filter papers were sufficiently dispersed in ethanol by using an ultrasonic washing machine for 30 minutes. The calcium phosphates fine particles-dispersed ethanol solution was whitely turbid.

Drops of the whitely turbid calcium phosphates fine particles-dispersed ethanol solution were put on a polystyrene substrate by using a dropper. After drying, the surface of the particles was observed through SEM.

From 50 ml of the calcium phosphates fine particles-dispersed ethanol solution, ethanol was removed by using an evaporator and replaced by 50 ml of 1% HCl aqueous solution. Thereafter, concentrations of Ca ions and P ions in the resulting solution were measured by ICP (calibration curve method).

To 100 ml of the calcium phosphates fine particles-dispersed ethanol solution was added 100 ml of distilled water. Thereafter, an ethanol content of the resulting solution was evaporated through an evaporator, so that calcium phosphates fine particles (apatite seeds) were dispersed in the distilled water. The thus obtained calcium phosphates fine particles-dispersed aqueous solution was divided in two screw cap bottles, 50 ml each. To the calcium phosphates fine particles-dispersed aqueous solution contained in one of the bottles was added 20 µl of PLA fine particles-dispersed aqueous solution (purchased from COREFRONT Corporation; product number: 11-00-203) having a particle diameter of 2 µm. To the calcium phosphates fine particles-dispersed aqueous solution contained in the other bottle was added 20 µl of collagen (product obtained by coating polystyrene/copolymerized polymer particles with collagen) fine particles-dispersed aqueous solution (product name: micromer; purchased from COREFRONT Corporation; product number: 01-25-104) having a particle diameter of 10 µm. In this manner, seeding on the surfaces of the respective fine particles were carried out. A period for seeding was one day.

After the seeding, the fine particles subjected to seeding were immersed in 1.0SBF as in Example 14 above, so that hydroxyapatites were grown.

Figure 27:
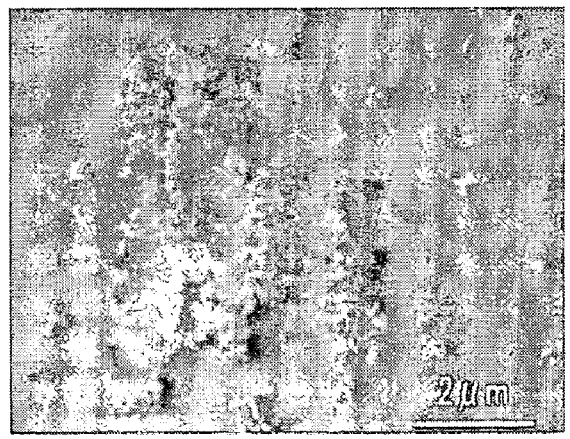
FIG. 27 is a scanning electron micrograph of calcium phosphates fine particles in a calcium phosphates fine particles-dispersed ethanol solution in Example 15 of the present invention.

The calcium phosphates fine particles-dispersed ethanol solution was dropped on a polystyrene substrate. FIG. 27 shows an SEM image of the surface of the particle after dried. Through the SEM observation, it was found that calcium phosphates fine particles collected by a polycarbonate filter paper having a pore diameter of 0.05 µm had a size approximately in the range from 100 nm to 200 nm.

Table 2 shows IPC measurement results. It was found that a yield was extremely increased, as compared with the yield obtained by the multistep filtration, i.e. approximately 0.12 mg at the maximum in the amount of hydroxyapatite (HAp) obtained. In Table 2, measurement results of Experiment 1 and Experiment 2 are results of the same measurements performed twice.

TABLE 2

|  | Ca ions (ppm) | P ions (ppm) | HAp (mg) |
| --- | --- | --- | --- |
| Experiment 1 | 14.4280 | 8.11826 | 1.808311 |
| Experiment 2 | 16.4561 | 9.19258 | 2.0625 |

Figure 28:
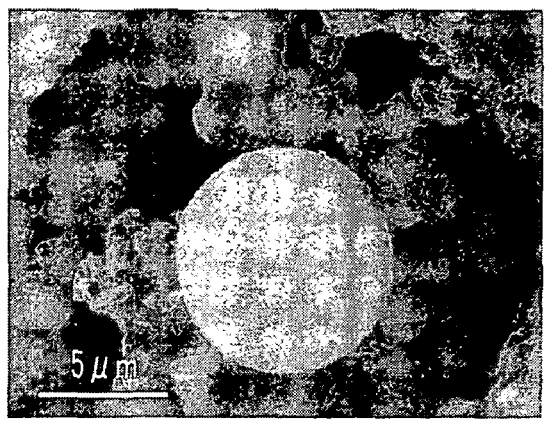
FIG. 28(a) is a scanning electron micrograph showing the result of the growth of hydroxyapatites by using a PLA fine particle as a base material in Example 15 of the present invention.
FIG. 28(b) is a scanning electron micrograph showing the result of the growth of hydroxyapatites by using a PLA fine particle as a base material in Example 15 of the present invention.
FIG. 28(c) is a chart of EDX analysis result of the growth of hydroxyapatites by using a PLA fine particle as a base material in Example 15 of the present invention.
Figure 28:
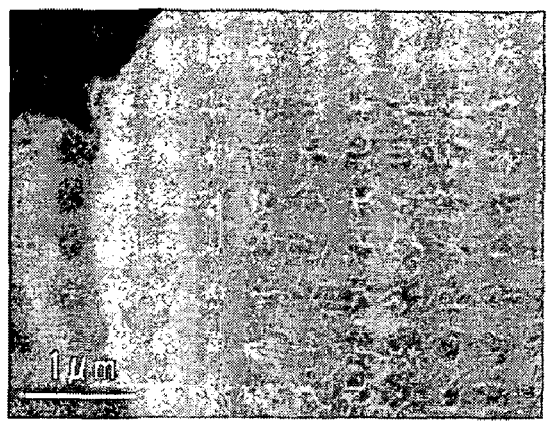
Figure 28:
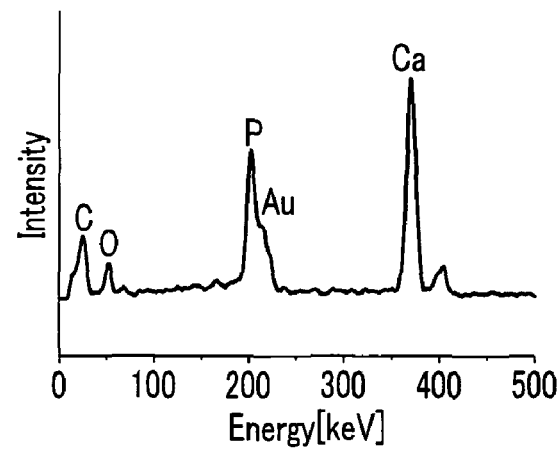

FIGS. 28(a) and 28(b) show SEM images of the surface of the PLA fine particle, and FIG. 28(c) shows EDX analysis result thereof. It was found that hydroxyapatites were grown uniformly on the surface of the PLA fine particle and a thin film of hydroxyapatites was formed.

Figure 29:
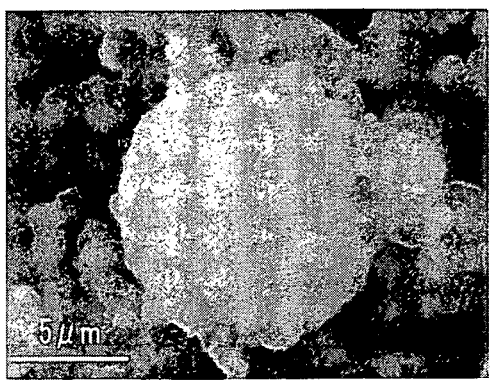
FIG. 29(a) is a scanning electron micrograph showing the result of the growth of hydroxyapatites by using a collagen fine particle as a base material in Example 15 of the present invention.
FIG. 29(b) is a scanning electron micrograph showing the result of the growth of hydroxyapatites by using a collagen fine particle as a base material in Example 15 of the present invention.
FIG. 29(c) is a chart of EDX analysis result of the growth of hydroxyapatites by using a collagen fine particle as a base material in Example 15 of the present invention.
Figure 29:
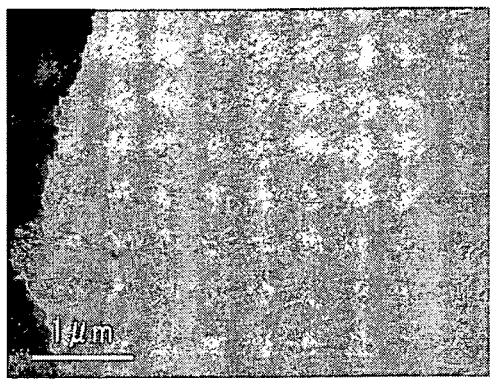
Figure 29:
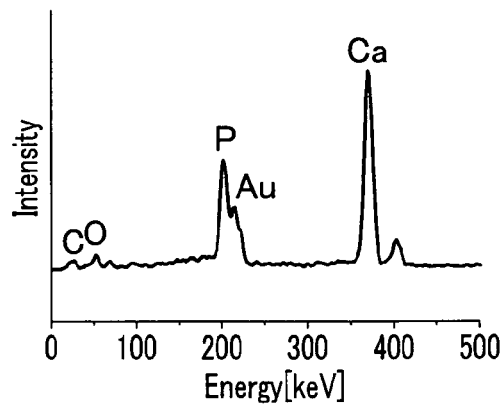

FIGS. 29(a) and 29(b) show SEM images of the surface of the collagen fine particle, and FIG. 29(c) shows EDX analysis result thereof. It was found that hydroxyapatites were grown uniformly on the surface of the PLA fine particle and a thin film of hydroxyapatites was formed.

Example 16

It was examined whether the change in concentration of the calcium phosphates fine particles in the calcium phosphates fine particles-dispersed solution had influence on the growth of hydroxyapatites after the seeding.

1000 ml of 1.0SBF was adjusted to be pH 8.5 by addition of tris(hydroxymethyl)aminomethane at 25° C. Right after the adjustment, the resulting solution was filtered through a hydrophilic PTFE-type filter paper having a pore diameter of 0.05 μm. After the filtration, NaCl was removed by passing distilled water through the filter paper, and moisture was then removed by passing ethanol through the filter paper. Thereafter, the filter paper was immersed in 200 ml of ethanol contained in a polystyrene screw cap bottle, and calcium phosphates fine particles on the surface of the filter paper were sufficiently dispersed in ethanol by using an ultrasonic washing machine for 30 minutes.

The calcium phosphates fine particles-dispersed ethanol solution was divided into four types of solutions respectively having volumes as shown in Table 3. Ethanol was removed from each of the solutions by using an evaporator, and substituted by 50 ml of distilled water. As a result, four types of calcium phosphates fine particles-dispersed aqueous solutions respectively having conditions 1 through 4 were obtained.

TABLE 3

| | Dilution rate | Ethanol | Distilled water |
|---|---|---|---|
| Condition 1 | 1/3 | 17 ml | 50 ml |
| Condition 2 | 1/10 | 5 ml | 50 ml |
| Condition 3 | 1/30 | 1.7 ml | 50 ml |
| Condition 4 | 1/100 | 0.5 ml | 50 ml |

To each of the calcium phosphates fine particles dispersion aqueous solutions was added 20 μl of PLA fine particles dispersion aqueous solution (purchased from COREFRONT Corporation; product number: 11-00-203) having a particle diameter of 2 μm, so that seeding around the PLA fine particle was carried out. A period for seeding was one day.

After the seeding, the PLA fine particles subjected to seeding were immersed in 1.0SBF as in Example 14 above, so that hydroxyapatites were grown.

Figure 30:
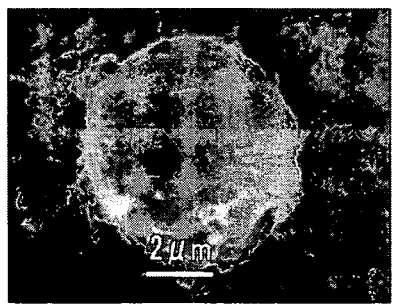
FIG. 30(a) is a scanning electron micrograph showing the surface of a PLA fine particle under Condition 1 in Example 16 of the present invention.
FIG. 30(b) is a chart showing EDX analysis result of the surface of the PLA fine particle under Condition 1 in Example 16 of the present invention.
Figure 30:
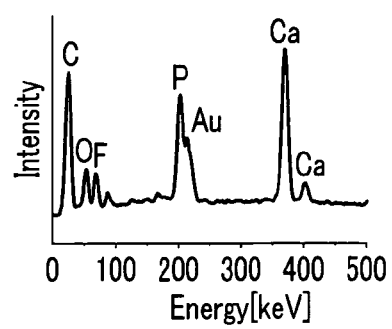

FIG. 30(a) shows an SEM image of the surface of the PLA fine particle under the condition 1, and FIG. 30(b) shows EDX analysis result thereof. It was found that hydroxyapatites were grown uniformly on the surface of the PLA fine particle, and a thin film of hydroxyapatites was formed.

Figure 31:
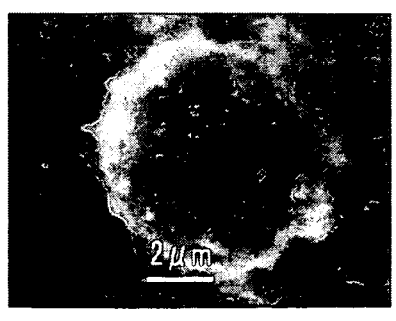
FIG. 31(a) is a scanning electron micrograph showing the surface of a PLA fine particle under Condition 2 in Example 16 of the present invention.
FIG. 31(b) is a chart showing EDX analysis result of the surface of the PLA fine particle under Condition 2 in Example 16 of the present invention.
Figure 31:
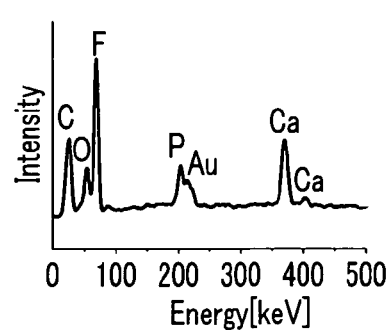

FIG. 31(a) shows an SEM image of the surface of the PLA fine particle under the condition 2, and FIG. 31(b) shows EDX analysis result thereof. It was found that hydroxyapatites were grown uniformly on the surface of the PLA fine particle, and a thin film of hydroxyapatites was formed.

Figure 32:
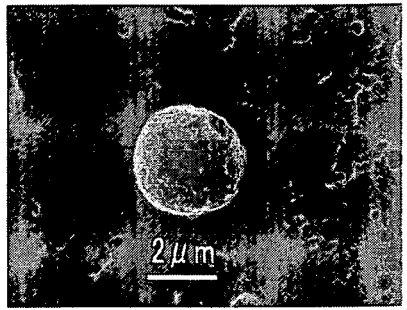
FIG. 32(a) is a scanning electron micrograph showing the surface of a PLA fine particle under Condition 3 in Example 16 of the present invention.
FIG. 32(b) is a chart showing EDX analysis result of the surface of the PLA fine particle under Condition 3 in Example 16 of the present invention.
Figure 32:
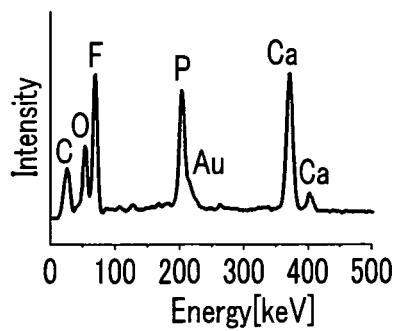

FIG. 32(a) shows an SEM image of the surface of the PLA fine particle under the condition 3, and FIG. 32(b) shows EDX analysis result thereof. It was found that hydroxyapatites were grown uniformly on the surface of the PLA fine particle, and a thin film of hydroxyapatites was formed.

Figure 33:
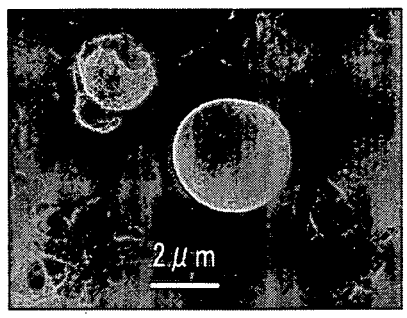
FIG. 33(a) is a scanning electron micrograph showing the surface of a PLA fine particle under Condition 3 in Example 16 of the present invention.
FIG. 33(b) is a chart showing EDX analysis result of the surface of the PLA fine particle under Condition 3 in Example 16 of the present invention.
Figure 33:
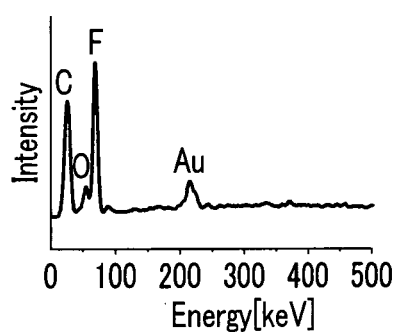

FIG. 33(a) shows an SEM image of the surface of the other PLA fine particle under the condition 3, and FIG. 33(b) shows EDX analysis result thereof. It was found that no hydroxyapatites were grown on the surface of the PLA fine particle, and a thin film of hydroxyapatites was not therefore formed.

Figure 34:
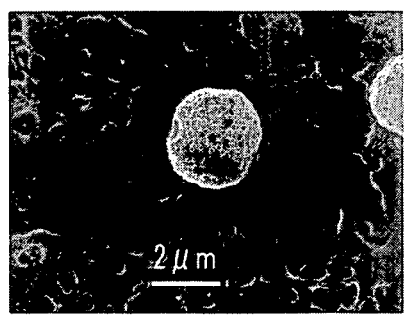
FIG. 34(a) is a scanning electron micrograph showing the surface of a PLA fine particle under Condition 4 in Example 16 of the present invention.
FIG. 34(b) is a chart showing EDX analysis result of the surface of the PLA fine particle under Condition 4 in Example 16 of the present invention.
Figure 34:
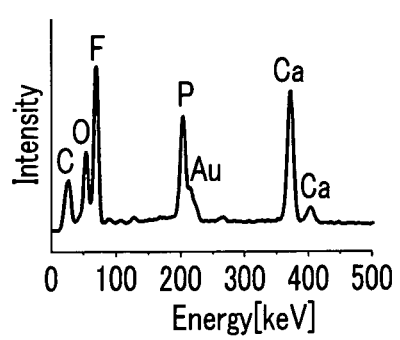

FIG. 34(a) shows an SEM image of the surface of the PLA fine particle under the condition 4, and FIG. 34(b) shows EDX analysis result thereof. It was found that hydroxyapatites were grown uniformly on the surface of the PLA fine particle, and a thin film of hydroxyapatites was formed.

Figure 35:
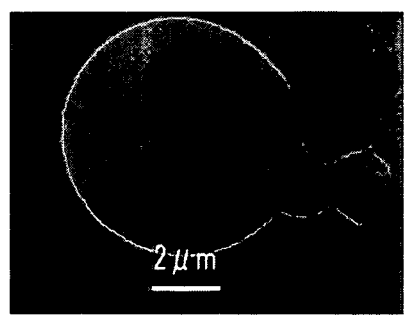
FIG. 35(a) is a scanning electron micrograph showing the surface of a PLA fine particle under Condition 4 in Example 16 of the present invention.
FIG. 35(b) is a chart showing EDX analysis result of the surface of the PLA fine particle under Condition 4 in Example 16 of the present invention.
Figure 35:
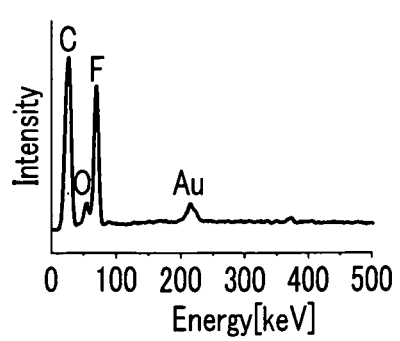

FIG. 35(a) shows an SEM image of the surface of the other PLA fine particle under the condition 4, and FIG. 35(b) shows EDX analysis result thereof. It was found that no hydroxyapatites were grown on the surface of the PLA fine particle, and a thin film of hydroxyapatites was not therefore formed.

From the above results, it was found that in 1:3 to 1:10 dilutions, needle crystal of hydroxyapatites was formed on the surface of the PLA fine particle. On the other hand, it was found that in 1:30 dilution or lower rate of dilution, the number of fine particles having a thin film of hydroxyapatites formed around the surfaces of the PLA fine particles was almost the same as the number of fine particles without a thin film of hydroxyapatites. It is considered that this occurred because the number of calcium phosphates fine particles as seeds was low in the calcium phosphates fine particles-dispersed solution.

Example 17

The formation of calcium phosphates fine particles by ultrasonic irradiation was examined.

200 ml of 1.0SBF was subjected to ultrasonic irradiation by using a frequency-variant ultrasonic wave output device and a ceramic vibrator. The 1.0SBF was adjusted to be pH 7.70 at 36.5° C. At a frequency of 200 kHz and 50 watts of power, the 1.0SBF was irradiated with ultrasonic waves for 2 hours while the vibrator was immersed in the 1.0SBF.

Figure 36:
FIG. 36 is a diagram showing the timecourse examination of the generation of calcium phosphates fine particles in 1.0SBF (pH7.70) irradiated with ultrasonic waves in Example of the present invention on the basis of Tyndall phenomenon.
Figure 36:
Figure 36:
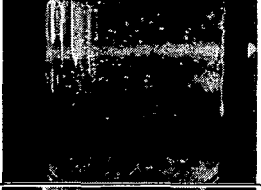
Figure 36:
Figure 36:
Figure 36:
Figure 36:
Figure 36:
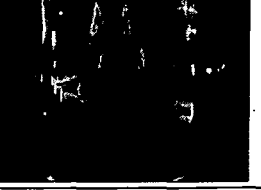

The results are shown in FIG. 36. Sample A is 1.0SBF which was irradiated with ultrasonic waves, and Sample B is 1.0SBF which was not irradiated with ultrasonic waves for comparison. Right after ultrasonic irradiation, it was found that Sample A became whitely turbid, and clear Tyndall phenomenon occurred therein. On the other hand, Tyndall phenomenon was not found in Sample B, which was not irradiated with ultrasonic waves.

In order to confirm that the white turbidity was not caused by mixing of ceramic flakes from the ceramic vibrator, 50 ml of Sample A right after the ultrasonic irradiation was filtered, and the substance obtained after the filtration was observed through SEM/EDX.

Figure 37A:
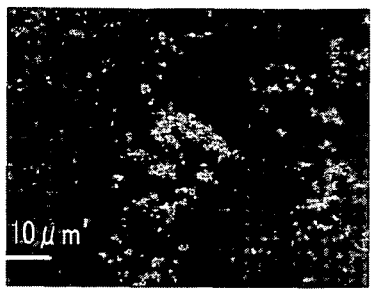
FIG. 37(a) is a scanning electron micrograph of a substance obtained after the filtration of 1.0SBF (pH7.70) right after ultrasonic irradiation in Example 17 of the present invention.
Figure 37B:
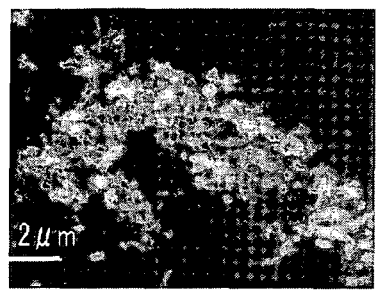
FIG. 37(b) is a scanning electron micrograph of a substance obtained after the filtration of 1.0SBF (pH7.70) right after ultrasonic irradiation in Example 17 of the present invention.
Figure 37C:
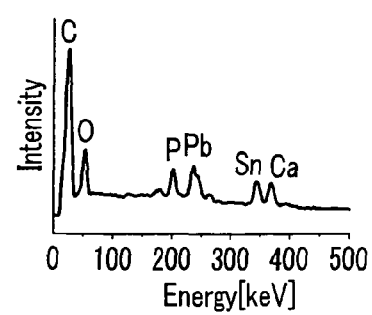
FIG. 37(c) is a chart showing EDX analysis result of a substance obtained after the filtration of 1.0SBF (pH7.70) right after ultrasonic irradiation in Example 17 of the present invention.

FIGS. 37(a) and 37(b) show SEM images of the substance obtained after the filtration of 1.0SBF (Sample A) right after the ultrasonic irradiation, and FIG. 37(c) show EDX analysis result thereof. In FIG. 37(c), peaks of Ca ions and P ions appeared, and precipitation of a substance considered to be calcium phosphate was found.

Figure 38A:
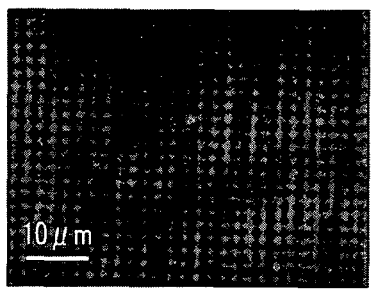
FIG. 38(a) is a scanning electron micrograph of a substance obtained after the filtration of 1.0SBF (pH7.70) which was not subjected to ultrasonic irradiation in Example 17 of the present invention.
Figure 38B:
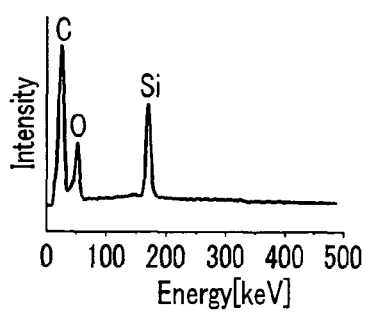
FIG. 38(b) is a chart showing EDX analysis result of a substance obtained after the filtration of 1.0SBF (pH7.70) which was not subjected to ultrasonic irradiation in Example 17 of the present invention.

FIG. 38(a) shows an SEM image of a substance obtained after the filtration of 1.0SBF (Sample B) without ultrasonic irradiation, and FIG. 37(b) shows EDX analysis result thereof. As is apparent from FIG. 38(a), nothing was found on the filter paper.

Specific embodiments or examples implemented in BEST MODE FOR CARRYING OUT THE INVENTION only show technical features of the present invention and are not intended to limit the scope of the invention. Variations can be effected within the spirit of the present invention and the scope of the following claims.

Industrial Applicability

As described above, the method according to the present invention is a method for stabilizing calcium phosphates fine particles by placing the calcium phosphates fine particles in an environment with a low inorganic ion concentration.

According to the above method, it is possible to stop the growth of the calcium phosphates fine particles by placing the calcium phosphates fine particles in an environment with low inorganic ion concentration. The calcium phosphates fine particles whose growth is stopped can be preserved for long periods while maintaining their solid phase forming activity high, and can be used suitably as seeds for the growth of calcium phosphates even after the preservation. The method for stabilizing calcium phosphates fine particles is a completely novel method that has never been reported, and very useful for its capability of easily manufacturing and preserving a large amount of calcium phosphates fine particles.

The present invention encompasses a method for manufacturing calcium phosphates fine particles including the above method as a step, calcium phosphates fine particles manufactured by such a manufacturing method, and a fine-particle-containing composition containing the calcium phosphates fine particles. The fine-particle-containing composition can be used in medical treatment and regeneration of teeth and bones.

A calcium-phosphates-containing composition according to the present invention manufactured using calcium phosphates fine particles as seeds are preferably used for a drug delivery system, a biosensor, a bioreactor, a medical device such as an artificial organ, an electronic device, an optical device, a magnetic material, a biodevice, and others.

A method for stabilizing calcium phosphates fine particles according to the present invention makes it possible to obtain a large amount of calcium phosphates fine particles having solid phase forming activity by a very easy and simple process and to preserve the calcium phosphates fine particles for long periods. Further, the calcium phosphates fine particles and a fine-particle-containing composition containing the calcium phosphates fine particles are suitably used especially in the medical field. Still further, a calcium-phosphates-containing composition manufactured by using the calcium phosphates fine particles can be preferably used in various kinds of fields, including the medical field.

The invention claimed is:

1. A manufacturing method for manufacturing seeds for growth of calcium phosphates, comprising:
   a first step of making calcium phosphates precipitated in an aqueous solution which is supersaturated with respect to calcium phosphates and in which no calcium phosphates are precipitated, wherein inorganic ion concentration, temperature, and/or pH of the aqueous solution is increased or a mechanical shock is given to the aqueous solution until precipitation of calcium phosphates is initiated; and
   a second step of, right after initiation of precipitation of calcium phosphates in the aqueous solution, stopping the growth of fine particles of calcium phosphates precipitated.

2. The manufacturing method as set forth in claim 1, wherein the second step is performed by lowering the inorganic ion concentration in the aqueous solution in which the fine particles are precipitated.

3. The manufacturing method as set forth in claim 2, the second step is performed by at least one operation selected from filtration, dilution, ion exchange, and centrifugation.

4. The manufacturing method as set forth in claim 1, wherein the second step is performed by lowering pH of the aqueous solution in which the fine particles are precipitated.

5. The manufacturing method as set forth in claim 4, wherein dialysis and/or filtration is further performed after the second step.

6. The manufacturing method as set forth in claim 1, wherein the second step is performed by separating the fine particles from the aqueous solution in which the fine particles are precipitated.

7. The manufacturing method as set forth in claim 6, wherein the fine particles are separated by filtration and/or centrifugation.

8. The manufacturing method as set forth in claim 1, wherein the inorganic ions are at least either calcium ions or hydrogenphosphate ions.

9. The manufacturing method as set forth in claim 1, wherein the mechanical shock is given by ultrasonic irradiation.

* * * * *